(12) United States Patent
Strecher et al.

(10) Patent No.: US 12,153,775 B2
(45) Date of Patent: Nov. 26, 2024

(54) ELECTRONIC DEVICES AND METHODS FOR SELF-AFFIRMATION AND DEVELOPMENT OF PURPOSEFUL BEHAVIOR

(71) Applicant: Kumanu, Inc., Ann Arbor, MI (US)

(72) Inventors: Victor Strecher, Ann Arbor, MI (US); Timothy Pituch, Ann Arbor, MI (US); Lisa Schutte, Ann Arbor, MI (US); Eric Zimmerman, San Anselmo, CA (US); Brandon Stange, West Bloomfield, MI (US); Haitham Maaieh, Ann Arbor, MI (US)

(73) Assignee: Kumanu, Inc., Ann Arbor, MI (US)

( * ) Notice: Subject to any disclaimer, the term of this patent is extended or adjusted under 35 U.S.C. 154(b) by 0 days.

(21) Appl. No.: 17/605,275

(22) PCT Filed: Apr. 23, 2020

(86) PCT No.: PCT/US2020/029451
§ 371 (c)(1),
(2) Date: Oct. 21, 2021

(87) PCT Pub. No.: WO2020/219631
PCT Pub. Date: Oct. 29, 2020

(65) Prior Publication Data
US 2022/0244818 A1     Aug. 4, 2022

Related U.S. Application Data

(60) Provisional application No. 62/838,016, filed on Apr. 24, 2019.

(51) Int. Cl.
*G06F 3/0482* (2013.01)
*G06F 9/451* (2018.01)
(Continued)

(52) U.S. Cl.
CPC ............ *G06F 3/0482* (2013.01); *G06F 9/451* (2018.02); *G06T 11/00* (2013.01); *G16H 20/70* (2018.01)

(58) Field of Classification Search
CPC ....... G06F 3/0482; G06F 9/451; G16H 20/70; G06T 11/00
See application file for complete search history.

(56) References Cited

U.S. PATENT DOCUMENTS

| 9,514,495 B2 * | 12/2016 | Erickson ............... G06F 16/285 |
| 2005/0287504 A1 * | 12/2005 | George .................. G09B 19/00 434/236 |

(Continued)

FOREIGN PATENT DOCUMENTS

| JP | 2008-250836 A | 10/2008 |
| JP | 2017-156850 A | 9/2017 |
| WO | 2018/048356 A1 | 3/2018 |

OTHER PUBLICATIONS

International Search Report dated Aug. 6, 2020, relating to International Application No. PCT/US 2020/029451.

(Continued)

*Primary Examiner* — Eric J. Bycer
(74) *Attorney, Agent, or Firm* — Honigman LLP; Grant Griffith

(57) ABSTRACT

A method and electronic device for self-affirmation and development of purposeful behavior includes displaying a purposeful inquiry interface including a plurality of navigation elements. The method also includes receiving a first navigation selection input corresponding to the first navigation element. The method further includes displaying explore interface including a plurality of explore interface elements. Each explore interface element corresponds to a particular activity. The method also includes receiving (Continued)

explore selection inputs. The method also includes storing data associated with the explore selection inputs.

18 Claims, 15 Drawing Sheets

(51) Int. Cl.
    *G06T 11/00*     (2006.01)
    *G16H 20/70*     (2018.01)

(56) References Cited

U.S. PATENT DOCUMENTS

| | | | | |
|---|---|---|---|---|
| 2005/0287505 | A1* | 12/2005 | George | G09B 19/00 434/236 |
| 2006/0205564 | A1* | 9/2006 | Peterson | A63B 69/00 482/8 |
| 2007/0117634 | A1 | 5/2007 | Hamilton et al. | |
| 2009/0012925 | A1* | 1/2009 | Brown | G06N 5/02 709/204 |
| 2010/0235776 | A1* | 9/2010 | Brown | G06Q 10/10 709/224 |
| 2012/0089909 | A1* | 4/2012 | Block | G06Q 10/06 715/764 |
| 2012/0244504 | A1* | 9/2012 | Wasserman | G09B 19/00 434/238 |
| 2012/0317064 | A1* | 12/2012 | Hagiwara | A61B 5/6898 706/46 |
| 2013/0060604 | A1* | 3/2013 | Wright | G06Q 30/02 705/7.32 |
| 2014/0032234 | A1* | 1/2014 | Anderson | A61B 5/0022 600/595 |
| 2014/0157171 | A1* | 6/2014 | Brust | G06F 3/0481 715/771 |
| 2014/0222719 | A1* | 8/2014 | Poulin | G16Z 99/00 706/46 |
| 2014/0272845 | A1* | 9/2014 | Hendriks | G06Q 10/1093 434/236 |
| 2014/0279720 | A1* | 9/2014 | Bhatia | G06N 5/04 706/11 |
| 2014/0349260 | A1* | 11/2014 | Hill | G09B 7/00 434/236 |
| 2015/0074109 | A1* | 3/2015 | Erickson | G06Q 50/01 707/737 |
| 2015/0120633 | A1* | 4/2015 | Norlander | G16H 20/70 706/46 |
| 2015/0332149 | A1* | 11/2015 | Kolb | G06F 3/048 706/11 |
| 2015/0364057 | A1* | 12/2015 | Catani | G16H 10/60 434/262 |
| 2016/0057499 | A1* | 2/2016 | Foerster | H04N 21/4782 705/319 |
| 2016/0074707 | A1* | 3/2016 | Thorpe | G09B 19/0092 434/247 |
| 2016/0140320 | A1* | 5/2016 | Moturu | G16H 20/70 434/236 |
| 2016/0314705 | A1* | 10/2016 | Segal | G06Q 10/0639 |
| 2017/0132395 | A1* | 5/2017 | Futch | G06Q 40/08 |
| 2017/0301255 | A1* | 10/2017 | Lee | G16H 40/63 |
| 2017/0329490 | A1 | 11/2017 | Esinovskaya et al. | |
| 2017/0329933 | A1* | 11/2017 | Brust | G06F 16/24575 |
| 2018/0256078 | A1 | 9/2018 | Vaterlaus | |
| 2019/0027052 | A1* | 1/2019 | Moore | G09B 19/00 |
| 2019/0354766 | A1* | 11/2019 | Moore | G06V 20/46 |

OTHER PUBLICATIONS

Intellectual Property India, First Examination Report related to Application No. 202147048361, dated May 6, 2022.

JPO. Office Action relating to applicaiton No. JP 2021-560644, dated Dec. 15, 2022.

IP Australia. Examination Report No. 1 relating to application No. 2020263384, dated Oct. 6, 2022.

* cited by examiner

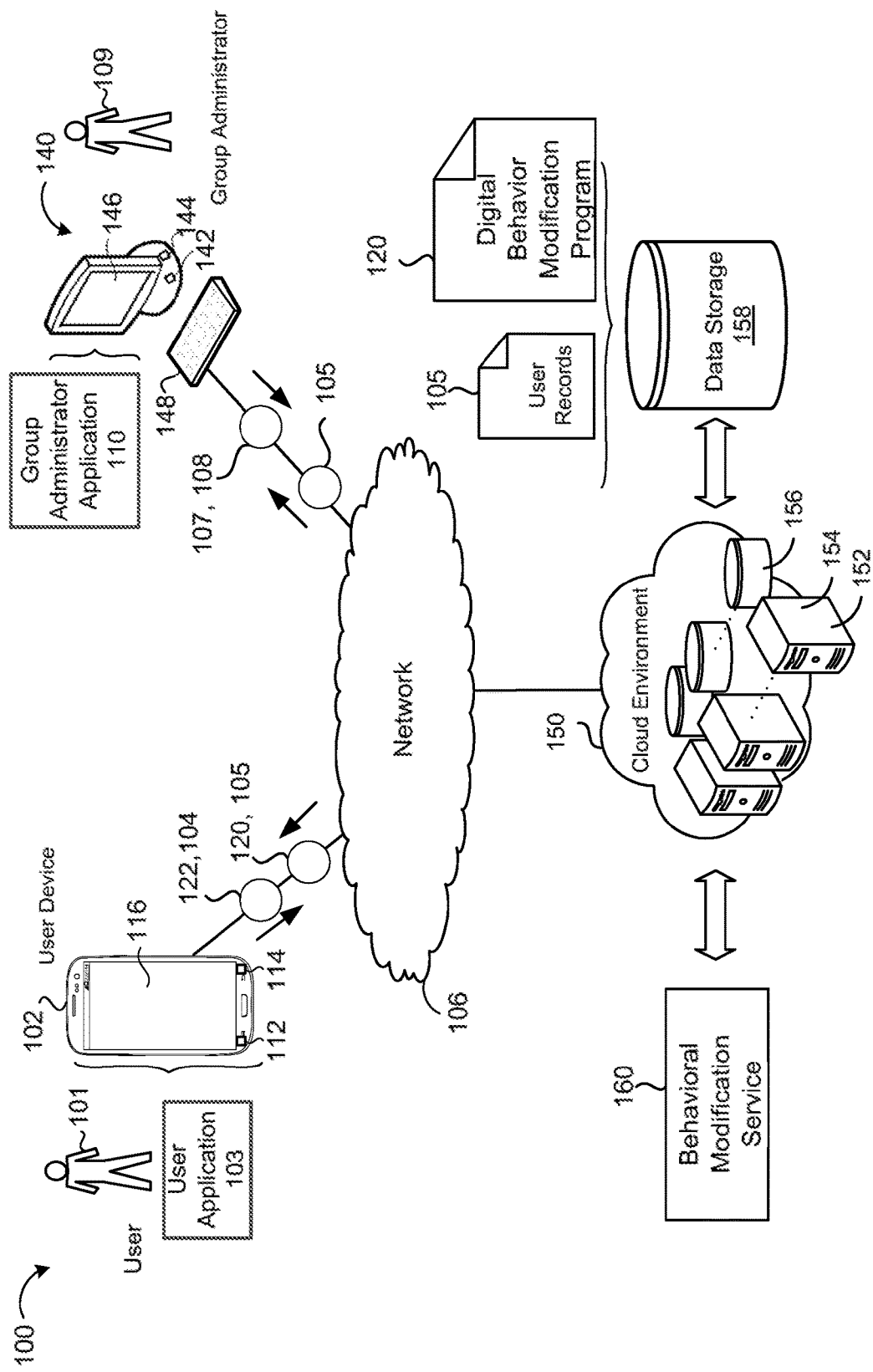

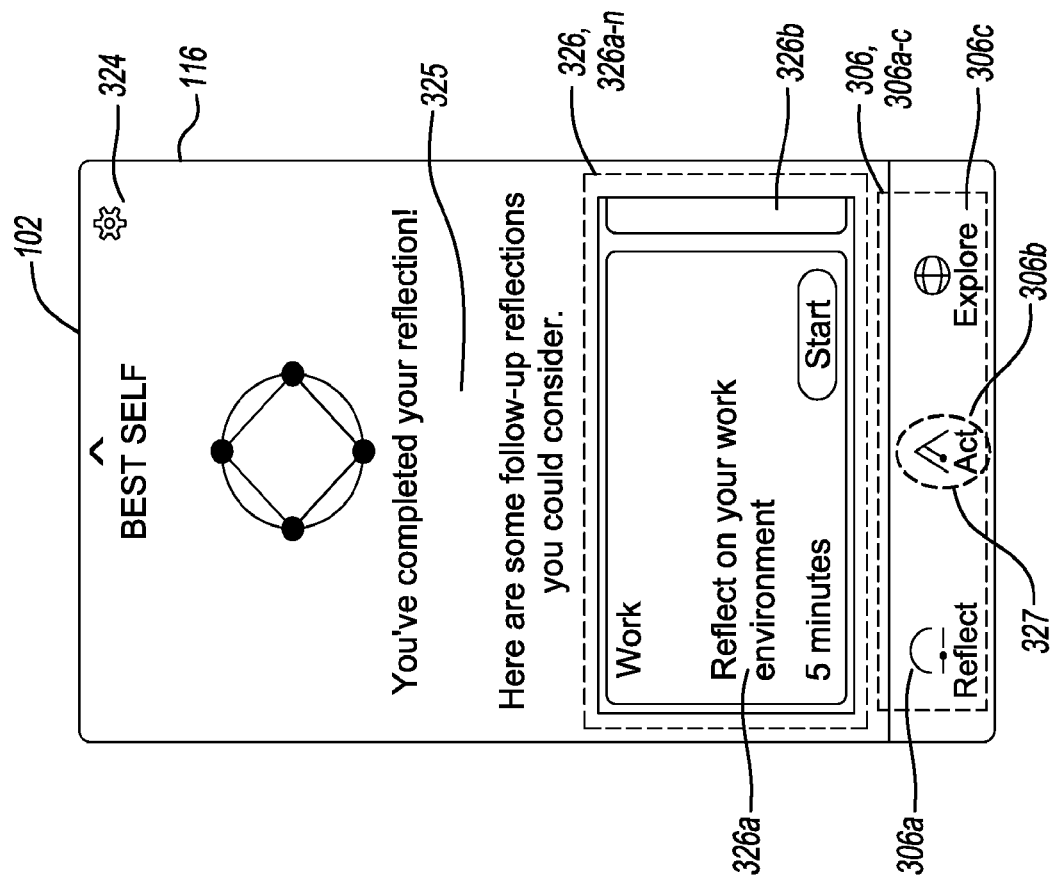

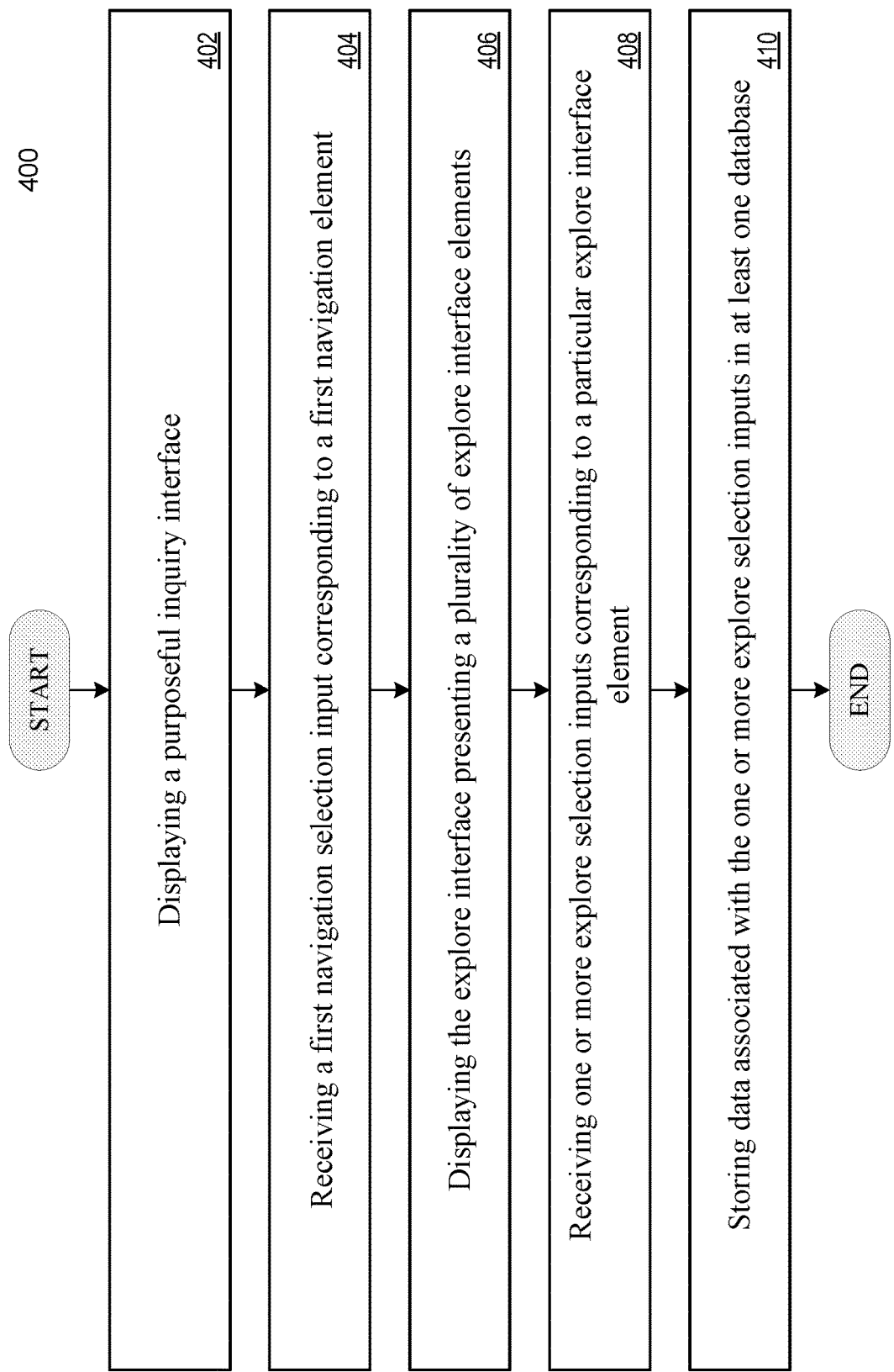

ELECTRONIC DEVICES AND METHODS FOR SELF-AFFIRMATION AND DEVELOPMENT OF PURPOSEFUL BEHAVIOR

CROSS REFERENCE TO RELATED APPLICATIONS

This patent application claims priority to U.S. Provisional Application 62/838,016, filed on Apr. 24, 2019, the disclosure of which is considered part of the disclosure of this application and is hereby incorporated by reference in its entirety.

TECHNICAL FIELD

This disclosure relates, generally, to self-affirmation and development of purposeful behavior, and more particularly, to electronic devices and methods for self-affirmation and development of purposeful behavior.

BACKGROUND

Living with purpose is facilitated by identifying one's best-self traits in a process known as self-affirmation. Focusing on an individual's purpose and best-self, through the process of self-affirmation, are associated with positive neurological impacts that are conducive to strong emotional self-regulation, positive feelings, and less defensiveness, leading to better behavioral outcomes in the individual. A best-self trait is a trait that brings out the best in an individual, allowing the individual to excel at daily tasks at school, work, home, or in other settings. Each individual may have a different best-self trait, or a best trait, and a different way of bringing out that trait. Each individual may also thrive better and live a more purposeful life by exhibiting a particular best-self trait. For example, an individual may have more purpose and feel more accomplished when they exhibit helpfulness in the form of helping others. Feeling more purposeful will help an individual to be happier and more productive in their daily lives.

Successfully forming habits that reflect an individual's best-self trait requires identification of purposeful behavior that may be in the form of activity-tracking and action-changing. It may be advantageous for an individual who wishes to align themselves with their best-self traits to identify what traits they would like to focus on, decide what activities can help the individual focus on that trait, and create habits out of those activities in order to do those activities periodically. For example, a student at school who wishes to be more helpful may want to become more helpful by tutoring their classmates every Friday afternoon.

Numerous scientific studies have documented the effect that a strong sense of purpose has on health outcomes, such as longevity, risk of cardiovascular diseases and Alzheimer's, resilience to stress and the ability to recover from both physical and mental illness; on life satisfaction and happiness; and on biological and neurological processes that intermediate both disease and behavior change. Studies show that thinking about one's purpose, or about one's values and strengths, through a process known as self-affirmation, reduces psychological defensiveness, increases openness to health and other messages, and improves the ability to making positive changes in behaviors. Further, interventions that pair a self-affirmation process with a perceived threat, such as an ego threat, along with the immediate availability of self-improvement resources, produce superior behavioral outcomes, as compared to self-affirmation interventions that lack one or more of these components.

An employer, group supervisor, or other type of group administrator may want to encourage their employees or group members to live purposeful lives and align with their best selves. As an employer, group supervisor, or other type of group administrator, learning about their employees' or group members' best traits may help the employer, group supervisor, or group administrator offer the resources that the employees or group members need to be able to align with their best selves and live purposeful lives.

There is thus a widely recognized need for improvement in the pertinent art.

SUMMARY

The instant disclosure provides various electronic devices and methods for identification of purposeful behavior. One aspect of the disclosure provides a method. The method includes, displaying, on a display of an electronic device, a plurality of navigation elements. Each of the plurality of navigation elements may correspond to a self-affirmation activity. The plurality of navigation elements includes a first navigation element corresponding to an explore interface. The method further includes receiving, at data processing hardware, a first navigation selection input. The first navigation selection input corresponds to the first navigation element. The method further includes displaying, on the display, the explore interface. The explore interface includes a plurality of explore interface elements. Each explore interface element corresponds to a particular activity. The method further includes receiving, at the data processing hardware, one or more explore selection inputs. The one or more explore selection inputs correspond to a particular explore interface element. The method further includes storing, at memory in communication with the data processing hardware, data associated with the one or more explore selection inputs in at least one database.

Implementations of the disclosure may include one or more of the following features as well. In some implementations, the method further includes, in response to receiving the one or more explore selection inputs, generating for display, one or more actions list interface element. Each one or more actions list interface element may correspond to each of the one or more explore selection inputs.

In some implementations, the method further includes, in response to storing data associated with the one or more explore selection inputs, generating for display one or more new explore interface elements.

In some implementations, the one or more new explore interface elements are displayed when the explore interface is refreshed.

In some implementations, the method further includes, in response to receiving the one or more explore selection inputs, generating, for display, one or more new explore interface elements.

In some implementations, the one or more new explore interface elements are displayed when the explore interface is refreshed.

In some implementations, the at least one database includes an individualized dataset. The explore interface elements may be generated based on data from the individualized dataset.

In some implementations, the at least one database includes a group-level dataset. The explore interface elements may be generated based on artificial intelligence algorithms and data from the group-level dataset.

In some implementations, the plurality of navigation elements further includes a second navigation element. The second navigation element may correspond to an action interface.

In some implementations, the method further includes, responsive to receiving, via the input device, a second navigation selection input, displaying on the display, the action interface. The action interface may include one or more action interface elements. The one or more action interface elements may correspond to a particular activity.

In some implementations, the one or more action interface elements include the one or more actions list interface elements.

In some implementations, the at least one database includes an individualized dataset, and the one or more action interface elements include one or more AI-generated action interface elements. The one or more AI-generated action interface elements may be generated based on the individualized dataset.

In some implementations, the at least one database includes a group-level dataset, and the one or more action interface elements include one or more AI-generated action interface elements. The one or more AI-generated action interface elements may be generated based on the group-level dataset.

In some implementations, the plurality of navigation elements further includes a third navigation element. The third navigation element may correspond to a reflection interface.

In some implementations, the method further includes, responsive to receiving, via the input device, a third navigation selection input, displaying on the display, the reflection interface. The reflection interface may include a plurality of reflection interface elements corresponding to a particular best trait. The plurality of reflection interface elements are generated using artificial intelligence algorithms.

In some implementations, the method further includes, receiving a reflection selection input. The reflection selection input may correspond to one or more of the plurality of reflection interface elements. The method may further include, in response to receiving the reflection selection input, storing data associated with the reflection selection input in the at least one database.

In some implementations, the plurality of reflection interface elements each correspond to a particular emotion.

In some implementations, the plurality of reflection interface elements each correspond to a particular best trait.

In some implementations, the method further includes displaying on the display, the reflection interface. The reflection interface may include a reflection textbox configured to accept free-form text input. The method may further include, in response to receiving a reflection textbox input, via the input device, storing data associated with the reflection textbox input in the at least one database.

In some implementations, the purposeful inquiry interface includes a welcome message. The welcome message may be generated based on data stored in the at least one database.

According to another aspect of the disclosure, a method is provided. The method includes displaying, on a display of an electronic device, a plurality of self-assessment interface elements. Each of the plurality of self-assessment interface elements correspond with a best trait. The method further includes receiving, at data processing hardware, one or more self-assessment selection inputs. The one or more self-assessment selection inputs correspond to a particular self-assessment interface element. The method further includes, storing, at a memory in communication with the data processing hardware, data associated with the one or more self-assessment selection inputs in at least one database. The method further includes displaying, on the display, a group-level visualization interface. The group-level visualization interface includes a plurality of best traits for a particular group.

This aspect of the disclosure may include one or more of the following features as well. In some implementations, the group-level visualization interface is updated in real time.

In some implementations, the plurality of best traits for the particular group is represented via word cloud.

In some implementations, the method further includes, in response to receiving the one or more self-assessment selection inputs, displaying on the display a constellation. The constellation may be generated based on data corresponding to the one or more self-assessment selection inputs.

According to another aspect of the disclosure, an electronic device for identification of purposeful behavior is provided. The electronic device includes a display, an input device, one or more processors, and memory in communication with the one or more processors and storing one or more programs that when executed on the one or more processors cause the one or more processors to perform operations. According to this aspect, the operations carry out a method. The method includes, displaying, on the display, a purposeful inquiry interface. The purposeful inquiry interface includes a plurality of navigation elements. Each of the plurality of navigation elements corresponds to a self-affirmation activity. The plurality of navigation elements includes a first navigation element corresponding to an explore interface. The method further includes, while displaying the purposeful inquiry interface, receiving, via the input device, a first navigation selection input. The first navigation selection input corresponds to the first navigation element. The method further includes, in response to receiving the first navigation selection input, displaying, on the display, the explore interface. The explore interface includes a plurality of explore interface elements. Each explore interface element corresponds to a particular activity. The method further includes, while displaying the explore interface, receiving, via the input device, one or more explore selection inputs. The one or more explore selection inputs correspond to a particular explore interface element. The method further includes, in response to receiving the one or more explore selection inputs, storing data associated with the one or more explore selection inputs in at least one database.

This aspect may include one or more of the following features as well. In some implementations, the operations implement a method that includes, in response to receiving the one or more explore selection inputs, generating for display, one or more actions list interface element. Each one or more actions list interface element corresponds to each of the one or more explore selection inputs. The method may further include, in response to storing data associated with the one or more explore selection inputs, generating for display one or more new explore interface elements.

In some implementations, the one or more new explore interface elements are displayed when the explore interface is refreshed.

In some implementations, the method further includes, in response to receiving the one or more explore selection inputs, generating, for display, one or more new explore interface elements.

In some implementations, the one or more new explore interface elements are displayed when the explore interface is refreshed.

In some implementations, the at least one database includes an individualized dataset. The explore interface elements may be generated based on data from the individualized dataset.

In some implementations, the at least one database includes a group-level dataset. The explore interface elements may be generated based on data from the group-level dataset.

In some implementations, the plurality of navigation elements further includes a second navigation element. The second navigation element may correspond to an action interface.

In some implementations, the method further includes, responsive to receiving, via the input device, a second navigation selection input, displaying on the display, the action interface. The action interface may include one or more action interface elements. The one or more action interface elements may correspond to a particular activity.

In some implementations, the one or more action interface elements include the one or more actions list interface elements.

In some implementations, the at least one database includes an individualized dataset, and the one or more action interface elements include one or more AI-generated action interface elements. The one or more AI-generated action interface elements may be generated based on the individualized dataset.

In some implementations, the at least one database includes a group-level dataset, and the one or more action interface elements include one or more AI-generated action interface elements. The one or more AI-generated action interface elements may be generated based on the group-level dataset.

In some implementations, the plurality of navigation elements further includes a third navigation element. The third navigation element may correspond to a reflection interface.

In some implementations, the method further includes, responsive to receiving, via the input device, a third navigation selection input, displaying on the display, the reflection interface. The reflection interface may include a plurality of reflection interface elements corresponding to a particular best trait.

In some implementations, the method further includes, receiving a reflection selection input. The reflection selection input may correspond to one or more of the plurality of reflection interface elements. The method may further include, in response to receiving the reflection selection input, storing data associated with the reflection selection input in the at least one database.

In some implementations, the plurality of reflection interface elements each correspond to a particular emotion.

In some implementations, the plurality of reflection interface elements each correspond to a particular best trait.

In some implementations, the method further includes displaying on the display, the reflection interface. The reflection interface may include a reflection textbox configured to accept free-form text input. The method may further include, in response to receiving a reflection textbox input, via the input device, storing data associated with the reflection textbox input in the at least one database.

In some implementations, the purposeful inquiry interface includes a welcome message. The welcome message may be generated based on data stored in the at least one database.

According to another aspect of the disclosure, an electronic device is provided. The electronic device includes a display, an input device, one or more processors, and memory in communication with the one or more processors and storing one or more programs that when executed on the one or more processors cause the one or more processors to perform operations. According to this aspect, the operations carry out a method. The method includes displaying, on the display, a self-assessment interface. The self-assessment interface includes a plurality of self-assessment interface elements. Each of the plurality of self-assessment interface elements correspond with a best trait. The method further includes, while displaying the self-assessment interface, receiving, via the input device, one or more self-assessment selection inputs. The one or more self-assessment selection inputs correspond to a particular self-assessment interface element. The method further includes, in response to receiving the one or more self-assessment selection inputs, storing data associated with the one or more self-assessment selection inputs in at least one database. The method further includes displaying, on the display, a group-level visualization interface. The group-level visualization interface includes a plurality of best traits for a particular group.

This aspect may include one or more of the following features as well. In some aspects, the operations implement a method that includes the group-level visualization interface updated in real time.

In some implementations, the plurality of best traits for the particular group is represented via word cloud.

In some implementations, the method further includes, in response to receiving the one or more self-assessment selection inputs. The method may also further include, displaying on the display, a constellation. The constellation may also be generated based on data corresponding to the one or more self-assessment selection inputs.

The details of one or more implementations of the disclosure are set forth in the accompanying drawings and the description below. Other aspects, features, and advantages will be apparent from the description and drawings, and from the claims.

DESCRIPTION OF DRAWINGS

Reference will now be made to the accompanying Figures, which are not necessarily drawn to scale, and wherein:

FIG. 1 is a schematic view of an example system implementing a computerized method for behavior analysis and best-self alignment in accordance with the principles of the present disclosure.

FIG. 3G illustrates a reflection elaboration interface in accordance with the principles of the present disclosure.

FIG. 3H illustrates a reflection completed interface in accordance with the principles of the present disclosure.

FIG. 4 is a flowchart illustrating a computerized method for identification of purposeful behavior in accordance with an exemplary embodiment of the disclosure.

Like reference symbols in the various drawings indicate like elements.

DETAILED DESCRIPTION

Figure 2B:
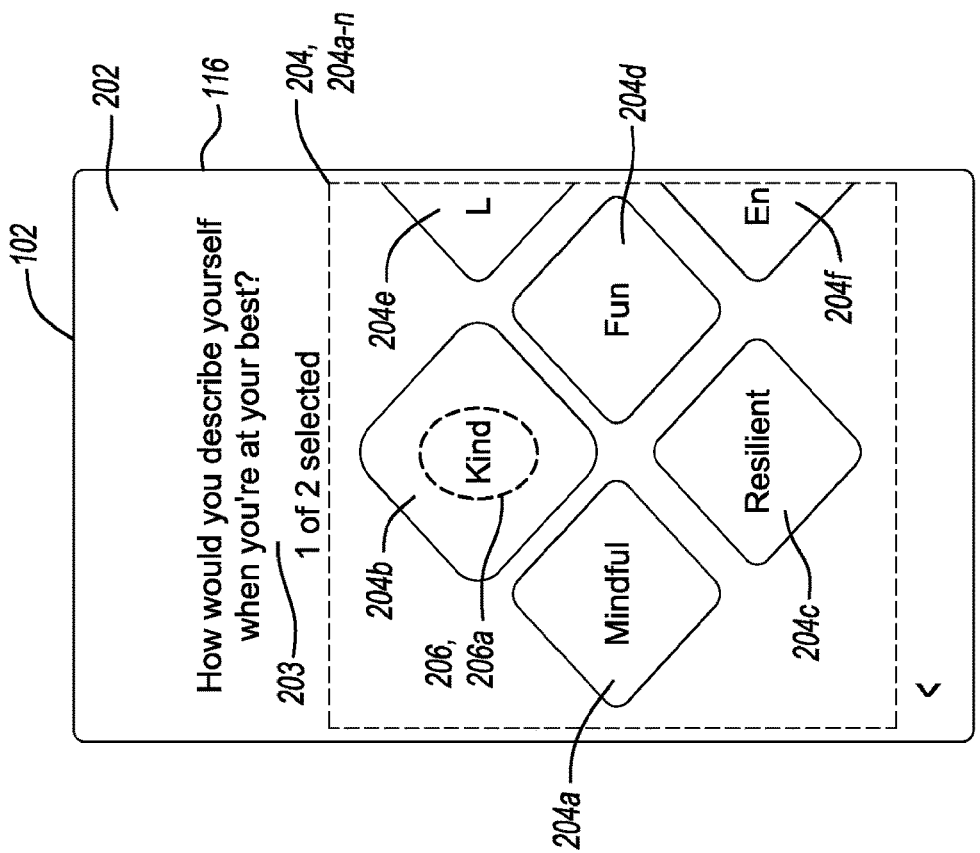
FIG. 2B illustrates another view of the best-self inquiry interface of FIG. 2A.

Some implementations of the disclosure will be described more fully with reference to the accompanying drawings. This disclosure may, however, be embodied in many different forms and should not be construed as limited to the implementations set forth herein.

Example implementations of the disclosure provide electronic devices and methods for identification of purposeful behavior.

Referring now to FIG. 1, in some implementations, an identification of purposeful behavior system 100 provides a user 101 access to a digital purposeful behavior program 120 and monitors events associated with the user's 101 interaction with the digital purposeful behavior program 120. Although the digital purposeful behavior program 120 is described as a subscription obtained from a group administrator, it is understood that, according to some implementations, the subscription will not require delegation from a group administrator. Rather, in such implementations, the digital purposeful behavior program 120 may be available to a user without a subscription from a group administrator, and the digital purposeful behavior program 120 nonetheless otherwise functions in accordance with the description of the digital purposeful behavior program 120 described herein.

As used herein, a digital purposeful behavior program may be referred to as a digital behavior program configured to deliver evidence-based psychosocial techniques for enabling a user to reach their full potential or to become their best self. In the instant case, the user 101 is a member of a group (e.g., a group of users 101). An authorized group administrator 109 (e.g., an employer, a resource group leader) supervising the user 101 may request or require the user 101 to subscribe to the digital purposeful behavior program 120 designed to help the user 101 identify best traits the user 101 wishes to align with in pursuit of aligning with their best selves. The group administrator 109 may be an employer, a church leader, a support-group supervisor, a parole officer, a youth-group leader, insurance provider, care giver, coach, administrator of an organization that user is a member of, or other supervising professional or individual who supervises or otherwise oversees the user 101.

In some examples, the system 100 includes a network 106, a user device 102, a group administrator system 140, and a purposeful behavior service 160. The network 106 provides access to cloud computing resources 150 (e.g., distributed systems) that execute the purposeful behavior service 160 to provide for the performance of services on remote devices. Accordingly, the network 106 allows for interaction between users 101 and group administrators 109 with the purposeful behavior service 160. For instance, the purposeful behavior service 160 may provide the user 101 access to the digital purposeful behavior program 120 and receive event data 122 inputted by the user 101 associated with the user's 101 interaction with the digital purposeful behavior program 120. In turn, the purposeful behavior service 160 may store the event data 122 on a storage system 156 of the cloud computing resources 150.

The network 106 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 106 may include one or more of a Wide Area Network (WAN), a Local Area Network (LAN), and a Personal Area Network (PAN). In some examples, the network 106 includes a combination of data networks, telecommunication networks, and a combination of data and telecommunication networks.

The user device 102, the group administrator system 140, and the purposeful behavior service 160 may communicate with each other by sending and receiving signals (wired or wireless) via the network 106. In some examples, the network 106 provides access to cloud computing resources, which may be elastic/on-demand computing and/or storage resources 156 available over the network 106. The term 'cloud' services generally refers to a service performed not locally on a user's device, but rather delivered from one or more remote devices accessible via one or more networks 20.

The user device 102 may include, but is not limited to, a portable electronic device (e.g., smartphone, cellular phone, personal digital assistant, personal computer, or wireless tablet device), a desktop computer, a smart speaker, or any other electronic device capable of sending and receiving information via the network 106. The user device 102 includes data processing hardware 112 (a computing device that executes instructions), memory hardware 114, and a display 116 in communication with the data processing hardware 112. In some examples, the user device 102 includes a keyboard 148, mouse, microphones, and/or a camera for allowing the user 101 to input data. In addition to or in lieu of the display 116, the user device 102 may include one or more speakers to output audio data to the user 101. For instance, a speaker may output audible alerts to notify the user 101 about some time sensitive event associated with the digital purposeful behavior program 120.

In some implementations, the user device 102 includes a user application 103 (or accesses a web-based user application) for establishing a connection with the purposeful behavior service 160 to access the digital purposeful behavior program 120. For instance, the user 101 may have access to the user application 103 for a duration (e.g., 12 months) of the digital purposeful behavior program 120. Here, the user device 102 may launch the user application 103 by initially providing an access code 104 that allows the user 101 to access content associated with the digital purposeful behavior program 120 from the purposeful behavior service 160 that is specifically tailored for enabling the user 101 to align with their best self through identification of purposeful behavior. The user application 103, when executed on the data processing hardware 112 of the user device 102, may display a variety of graphical user interfaces (GUIs) on the display 116 of the user device 102 that, among other things, allow the user 101 to input event data 122.

The storage resources 156 may provide data storage 158 (e.g., at least one database) for storing the event data 122 received from the user 101 in a corresponding user record 105 as well as the digital purposeful behavior program 120 that is subscribed to by the user 101. In some implementations, the data storage 158 may include an individualized dataset storing data (e.g., email address, name, best self traits, etc.) pertaining to an individual user 101, or a group-level dataset storing data (e.g., configurations, content, etc.) pertaining to a group of users 101. In some implementations, the data storage 158 is a single database storing data pertaining to an individual user 101, or a group of users 101, in one or more data sets. In other implementations, the data storage 158 is a plurality of databases, each database including one or more data sets corresponding to an individual user 101 or a group of users 101.

The user record 105 may be encrypted while stored in the data storage 158, but may later be de-crypted when the user 101 requests the user record 105 (assuming the requester is authorized/authenticated to access the user record 105). All data transmitted over the network 106 between the user device 102 and the cloud computing system 150 may be encrypted and sent over secure communication channels. For instance, the user application 103 may encrypt the event data 122 before transmitting to the purposeful behavior service 160 via the HTTPS protocol and decrypt a user record 105 received from the purposeful behavior service 160. When network connectivity is not available, the user application 103 may store the event data 122 in an encrypted queue within the memory hardware 114 until network connectivity is available.

The group administrator system 140 may be located at an employer's place of business, supervisor's office, or facility administered by the group administrator 109 and may include data processing hardware 142, memory hardware 144, and a display 146. The memory hardware 144 and the display 146 are in communication with the data processing hardware 142. For instance, the data processing hardware 142 may reside on a desktop computer or portable electronic device for allowing the group administrator 109 to input and retrieve data (e.g., data aggregated for a plurality of users 101) to and from the purposeful behavior service 160.

In some examples, the group administrator 109 may initially transmit data 107 (e.g., name, date of employment, title, etc.) corresponding to one or more particular users 101 at the time the group administrator suggests, requests or requires such user(s) 101 to subscribe to the digital purposeful behavior program 120. The group administrator system 140 may include a keyboard 148, mouse, microphones, speakers and/or a camera.

In some implementations, the group administrator system 140 (i.e., via the data processing hardware 142) includes a group administrator application 110 (or accesses a web-based user application) for establishing a connection with the purposeful behavior service 160 to input and retrieve data therefrom. For instance, the group administrator system 140 may access aggregated, anonymized user records 105 securely stored by the purposeful behavior service 160 on the storage resources 156 by providing an authentication token 108 validating that the group administrator 109 is authorized to access the corresponding aggregated, anonymized user records 105. The authentication token 108 may identify a particular group membership of the group administrator 109 and the aggregated, anonymized user records 105 that the group administrator system 140 is permitted to obtain from the purposeful behavior service 160. In some implementations, the group administrator 109 does not have access to any user's 101 individual data or entries and the group administrator 109 is unable to track any individual user's 101 usage or access of the user application 103. The user records 105 may include time-stamped event data 122 indicating the user's interaction with the digital purposeful behavior program 120 through the user application 103 executed on the user device 102. In some implementations, time-stamped event data 122 of the user records 105 is anonymized.

The cloud computing resources 150 may be a distributed system (e.g., remote environment) having scalable/elastic resources 152. The resources 152 include computing resources 154 (e.g., data processing hardware) and/or the storage resources 156 (e.g., memory hardware). The cloud computing resources 150 execute the purposeful behavior service 160 for facilitating communications with the user device 102 and the group administrator system 140 and storing data on the storage resources 156 within the data storage 158. In some examples, purposeful behavior service 160 and the data storage 158 reside on a standalone computing device. The purposeful behavior service 160 may provide the user 101 with the user application 103 (e.g., a mobile application, a web-site application, or a downloadable program that includes a set of instructions) executable on the data processing hardware 112 and accessible through the network 106 via the user device 102 when the user 101 provides a valid access code 104. Similarly, the purposeful behavior service 160 may provide the group administrator 109 with the group administrator application 110 (e.g., a mobile application, a web-site application, or a downloadable program that includes a set of instructions) executable on the data processing hardware 142 and accessible through the network 106 via the group administrator system 140.

FIGS. 2A-3L illustrate schematic views of exemplary GUIs of the digital purposeful behavior program 120 (e.g., by execution of the user application 103) displayed on the display 116 of the user device 102 for enabling the user 101 to align with their best self through identification of purposeful behavior. As will be described in more detail below, the example GUIs may display graphical elements (e.g., buttons) that the user 101 may select via user inputs such as touch inputs, speech inputs, or other input techniques via a mouse, stylus, keyboard, gesture, or eye gaze, for example.

Figure 2A:
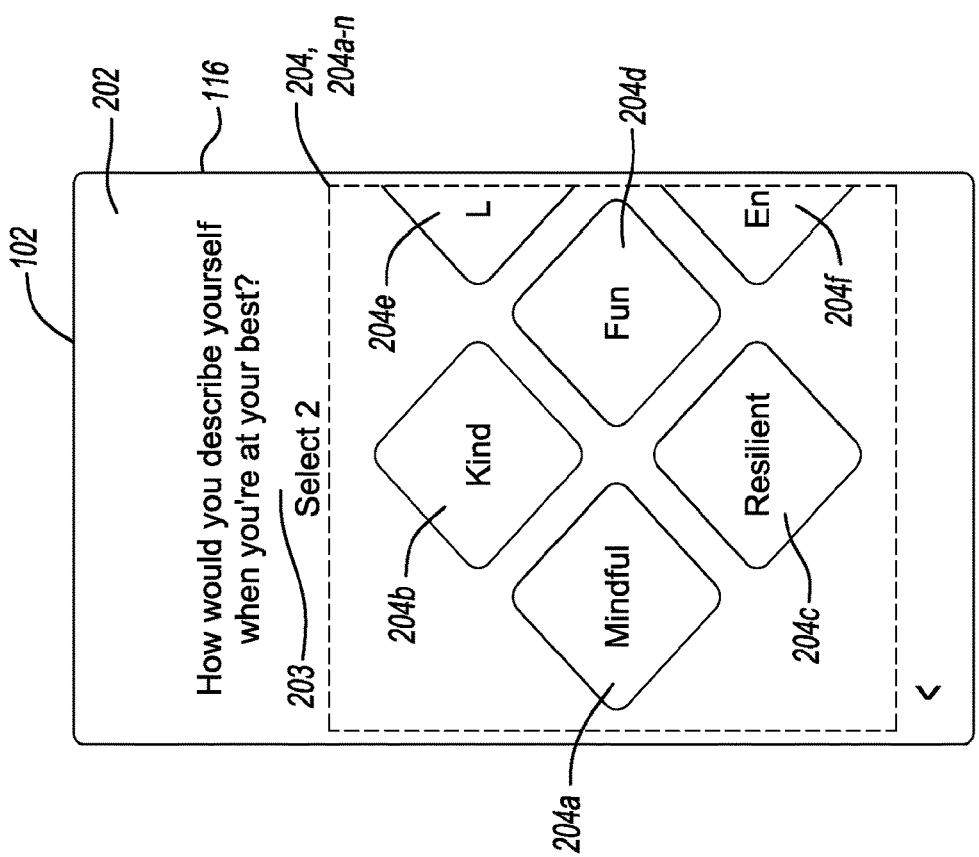
FIG. 2A illustrates a best-self inquiry interface in accordance with the principles of the present disclosure.
Figure 2D:
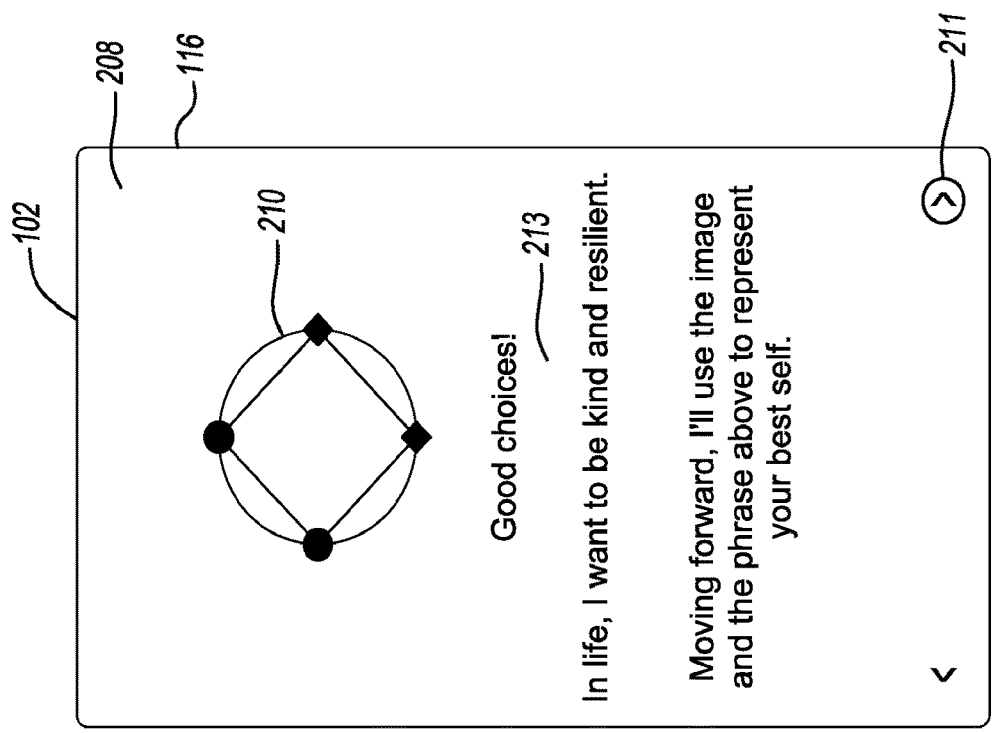
FIG. 2D illustrates a best-self recap interface in accordance with the principles of the present disclosure.
Figure 2C:
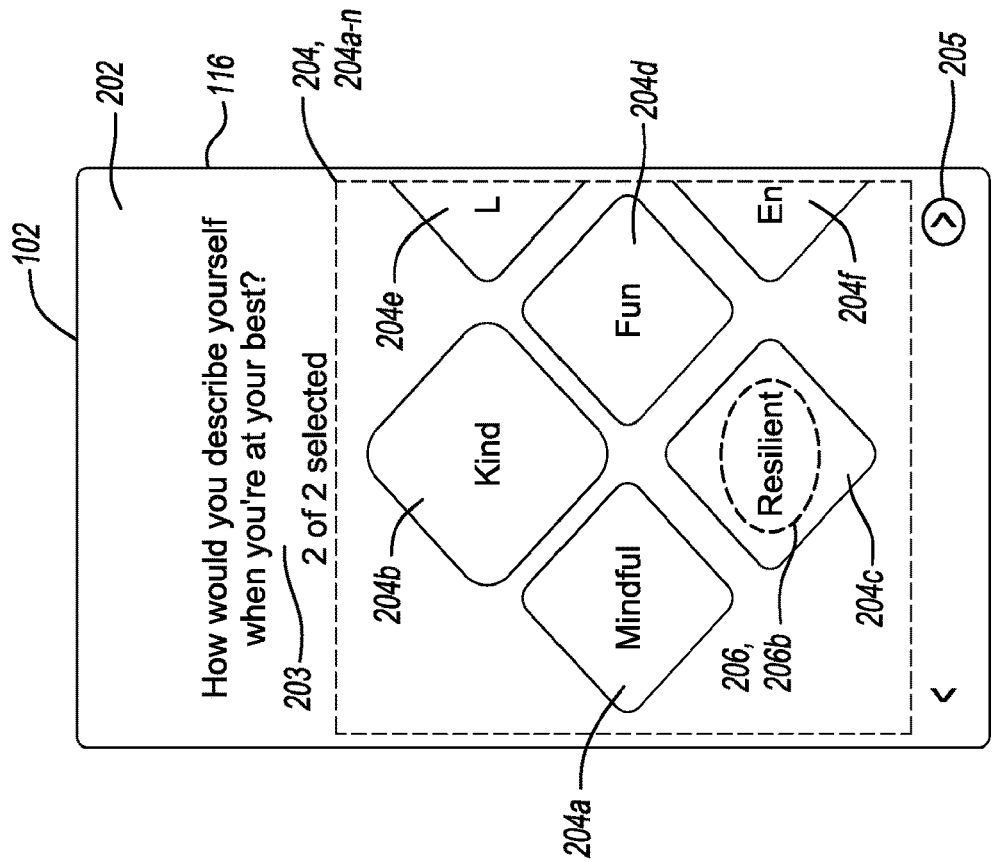
FIG. 2C illustrates another view of the best-self inquiry interface of FIG. 2A.

Referring to FIGS. 2A-2C, in some implementations, upon launching the user application 103 associated with the digital purposeful behavior program 120 that the user 101 subscribes to, the user application 103 displays a best-self inquiry GUI 202 that allows the user 101 to input a particular best trait they would use to describe themselves when they are at their best. Referring now to FIG. 2A, in the example shown, the best-self inquiry GUI 202 provides a plurality of selectable best-self inquiry interface elements 204 (e.g., buttons), each 204a-n associated with a corresponding best trait that the user 101 believes best describes them when they are at their best, or that the user 101 may wish to align themselves with in order to be at their best. A best-self trait, or best trait, is a trait that an individual may have that allows them to excel in a particular setting of their life, such as school, work, home, church group, support group, or other setting. Individuals who align with their best-self trait may feel that they are more purposeful in life, and may be productive in their lives as a result of their feeling of fulfillment. Examples of best-self traits include, but are not limited to, being kind, focused, resilient, hopeful, empathetic, optimistic, or any other trait that, when an individual demonstrates that trait, they align more with their best selves. Allowing the user 101 to browse and view possible best-self traits helps the user 101 identify their best-trait by narrowing down the unlimited possibilities of traits while singling out positive traits for the user 101 to select.

While the example shown depicts interface elements 204a-f, the user may view additional interface elements 204n by scrolling (e.g., via a swipe gesture) on the display 116 of the user device 102. In some embodiments, the plurality of best-self inquiry interface elements 204 may be prepopulated based on common traits that members of a general population believe to have when they are at his or best. In other embodiments, the plurality of best-self inquiry interface elements 204 may be prepopulated based on common traits shared by a plurality of users 101, such as members of a sub-group or organization for which the digital purposeful behavior program 120 is intended to be used. In some examples, the plurality of best-self inquiry interface elements 204 are randomized and displayed in a different order for each user 101. In other embodiments, the plurality of best-self inquiry interface elements 204 are generated based on information gathered on the user 101 and stored in data storage 158. For example, the plurality of best-self inquiry interface elements 204 may be generated and displayed for a particular user 101 using machine learning or artificial intelligence algorithms based on information gathered and stored in the data storage 158 for the particular user 101. In some implementations, the plurality of best-self inquiry interface elements 204 are generated based on information gathered and stored (e.g., in the data storage 158) on a group of which the user 101 is a member. For example, the plurality of best-self inquiry interface elements 204 may be generated using machine learning or artificial intelligence algorithms based on information gathered and stored in the data storage 158 for a group of users 101.

The best-self inquiry GUI 202 may provide instructions 203 (e.g., "How would you describe yourself when you're at your best?" and "Select 2"). Instructions 203 may prompt the user 101 to enter input corresponding to how the user 101 would describe themselves when they are at their best. Instructions 203 may also instruct the user 101 on how many best-self inquiry interface elements 204 to select. The user 101 may indicate how they would describe themselves when they are at their best by selecting the corresponding best-self inquiry interface element(s) 204 displayed in the best-self inquiry GUI 202. In the example shown, a first best-self inquiry interface element 204a ("Mindful") indicates that the user 101 would describe themselves as mindful when they are at their best. A second best-self inquiry interface element 204b ("Kind") indicates that the user 101 would describe themselves as kind when they are at their best. A third best-self inquiry interface element 204c ("Resilient") indicates that the user 101 would describe themselves as resilient when they are at their best. A fourth best-self inquiry interface element 204d ("Fun") indicates that the user 101 would describe themselves as fun when they are at their best. A fifth best-self inquiry interface element 204e ("Loving") indicates that the user 101 would describe themselves as loving when they are at their best. A sixth best-self inquiry interface element 204f ("Energetic") indicates that the user 101 would describe themselves as energetic when they are at their best.

The best-self inquiry interface elements 204a-204f do not represent an exhaustive list of all best-self inquiry interface elements, but rather an exemplary list of best-self inquiry interface elements that may be included as part of the best-self inquiry GUI 202. Furthermore, the best-self inquiry GUI 202 may include other best-inquiry interface elements in addition to best-self inquiry interface elements 204a-204f, or may omit one or more best-self inquiry interface elements 204a-204f, without departing from the teachings herein.

Referring now to FIG. 2B, in the example shown, the user device 102 detects a best-self inquiry selection input 206 (e.g., touch or spoken) corresponding to a particular best-self inquiry interface element 204a-n. In some implementations, the user device 102 detects only a single best-self inquiry selection input 206, corresponding to only one best-self inquiry interface element 204a-n. In other implementations, the user device 102 detects more than one best-self inquiry selection inputs 206 corresponding to more than one best-self inquiry interface elements 204a-n. For example, the user device 102 may detect up to "n" best-self inquiry selection inputs 206 corresponding to each best-self inquiry interface elements 204a-n. In the example shown, the user device 102 detects a first best-self inquiry selection input 206a corresponding to the best-self inquiry interface element 204b ("Kind") indicating the user 101 would describe themselves as kind when they are at their best. In some implementations, the first best-self inquiry selection input 206a causes the user application 103 to transmit time-stamped event data 122 to the purposeful behavior service 160 (FIG. 1) that includes a selection indication identifying that the user 101 believes they are at their best self when they are kind.

In some implementations, after detecting the first best-self inquiry selection input 206a, the user application 103 advances to display a best-self recap GUI 208 (FIG. 2D) on the display 116 of the user device 102. In other implementations, after detecting the first best-self inquiry selection input 206a, the user application 103 indicates selection of the selected best-self inquiry interface element. For example, as illustrated in FIG. 2B, the user application 103 may change the display (e.g., highlight, change color, display check mark, or otherwise indicate selection of the element) of the selected best-self inquiry interface element(s) 204a-n (e.g., element 204b) on the display 116, while continuing to display the best-self inquiry GUI 202. The user application 103 may also display an updated version of instructions 203 displaying a message confirming the user 101 has made a selection (e.g., "1 of 2 selected").

Referring now to FIG. 2C, in the example shown, the user device 102 detects a second best-self inquiry selection input 206b corresponding to the best-self inquiry interface element 204c ("Resilient") indicating the user 101 would describe themselves as resilient when they are at their best. In some implementations, the second best-self inquiry selection input 206b causes the user application 103 to transmit time-stamped event data 122 to the purposeful behavior service 160 (FIG. 1) that includes a selection indication identifying that the user 101 believes they are at their best self when they are resilient. The user application 103 may also display an updated version of instructions 203 displaying a message confirming the user 101 has made another selection (e.g., "2 of 2 selected").

In some examples, after detecting the second best-self inquiry selection input 206b, the user application 103 advances to the best-self recap GUI 208 (FIG. 2D) on the display 116 of the user device 102. In some configurations, detecting the second best-self inquiry selection input 206b causes the user application 103 to automatically display the best-self recap GUI 208. In other configurations, the user application 103 requires the user 101 to first confirm the selected best-self inquiry interface element 204 by selecting a confirmation element 205 (e.g., a button or arrow, as shown in FIG. 2C). In these configurations, the user application 103 displays the best-self recap GUI 208 in response to a selection of the confirmation element 205.

At FIG. 2D, in some configurations, the user application 103 causes the user device 102 to display the best-self recap GUI 208. The best-self recap GUI 208 may display a constellation image 210. The constellation image 210 may vary based on selection by the user 101 in the best-self inquiry GUI 202 (FIG. 2A). In some configurations, the constellation image 210 is randomized for each user 101. The display of the constellation image 210 on the best-self recap GUI 208 is exemplary, as the constellation image 210 may be present throughout any screen of the user application 103. The best-self recap GUI 208 may be beneficial for aligning the user 101 with their traits by reinforcing and reminding the user of their selection in the best-self inquiry GUI 202. In particular, the best-self recap GUI 208 may include a displayed confirmation message 213 having one or more words or messages corresponding to the best-self inquiry interface elements 204a-n. For example, as illustrated in FIG. 2D, the confirmation message 213 may include the words "Kind" and "Resilient," corresponding to the best-self inquiry interface elements 204b and 204c selected in the best-self inquiry GUI 202.

In some configurations, the user application 103 requires the user 101 to select a confirmation element 211 (e.g., a button or arrow, as shown in FIG. 2D) in order for the user application 103 to advance to display a group best-self recap GUI 212 (FIG. 2E) on the display 116 of the user device 102. In other configurations, the user application 103 advances to display the group best-self recap GUI 212 on the display 116 of the user device 102 after a short period of time (e.g., 10 seconds) has passed.

Figure 2F:
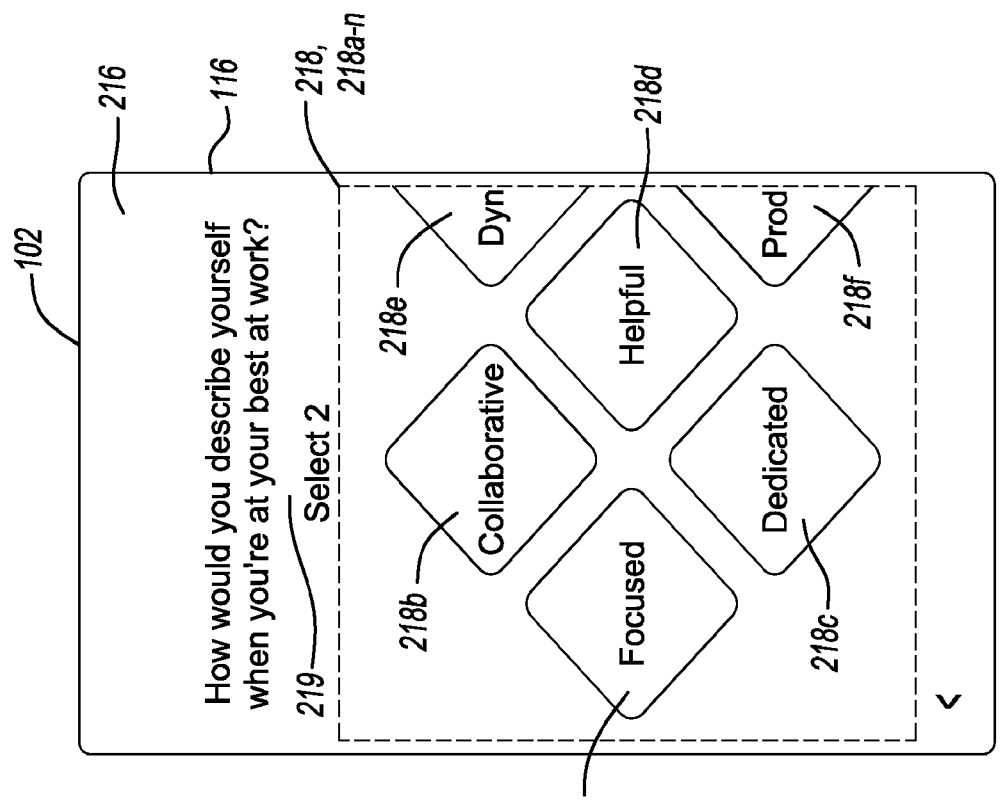
FIG. 2F illustrates a work inquiry interface in accordance with the principles of the present disclosure.
Figure 2E:
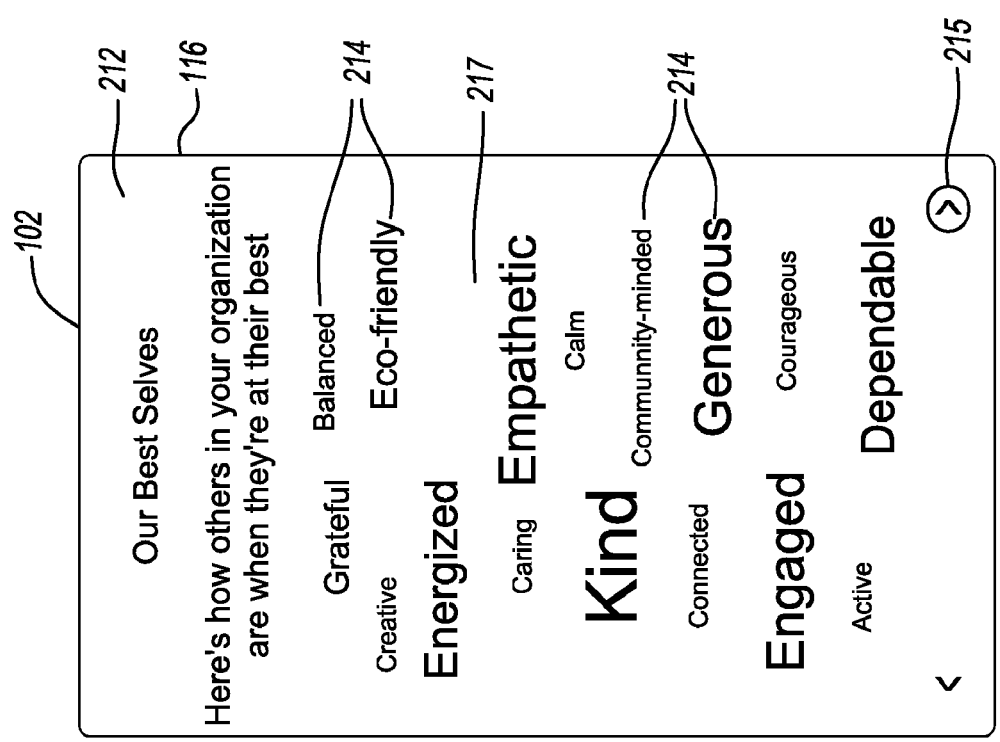
FIG. 2E illustrates a group best-self recap interface in accordance with the principles of the present disclosure.

At FIG. 2E, in some configurations, the user application 103 causes the user device 102 to display the group best-self recap GUI 212. The group best-self recap GUI 212 may present a plurality of best-self traits corresponding to a particular group. The group may be populated based on a sub-group, geographic population, or the full user population. In the example shown, the group best-self recap GUI 212 includes a displayed plurality of words 214 corresponding to best-self traits interface elements (e.g., best-self traits interface elements 204a-n). In some implementations, the words 214 are represented by a word cloud 217, where each word 214 in the word cloud 217 corresponds to a particular best trait, and the size of each word 214 corresponds to a frequency that the word was selected by an individual in the group. For example, each word 214 in the word cloud 217 may correspond to a particular best trait selected by one or more individuals in the group (e.g., one or more users 101) at the best-self traits interface elements 204a-n, and the size of each word 214 may correspond to a frequency that the word 214 was selected by an individual in the group at the best-self traits interface elements 204a-n. Though FIG. 2E depicts a display with plurality of words 214 represented by a word cloud 217 to represent the plurality of best-self traits corresponding to a group, it should be noted that the plurality of best-self traits may be represented via stacked ranked lists, graphs, or other method of data visualization. FIG. 2E may display data corresponding to the user's 101 place of employment, a particular department within the user's 101 place of employment, or a particular region such as the country, state, or area in which the user 101 resides, enabling the user 101 to see how their best-self traits align with multiple types of social groupings.

In some implementations, the plurality of words 214 is generated based on data entered by the particular group. In other implementations, the plurality of words 214 is generated using machine learning or artificial intelligence algorithms with data corresponding to data collected on a group using the application 103 and stored in the data storage 158. In some implementations, the plurality of words 214 is updated in real time. In some configurations, the user application 103 requires the user 101 to select a confirmation element 215 (e.g., a button or arrow, as shown in FIG. 2E) in order for the user application 103 to advance to display a work inquiry GUI 216 (FIG. 2F) on the display 116 of the user device 102. In other configurations, the user application 103 advances to the display work inquiry GUI 216 on the display 116 of the user device 102 after a short period of time (e.g., 10 seconds) has passed.

Figure 2H:
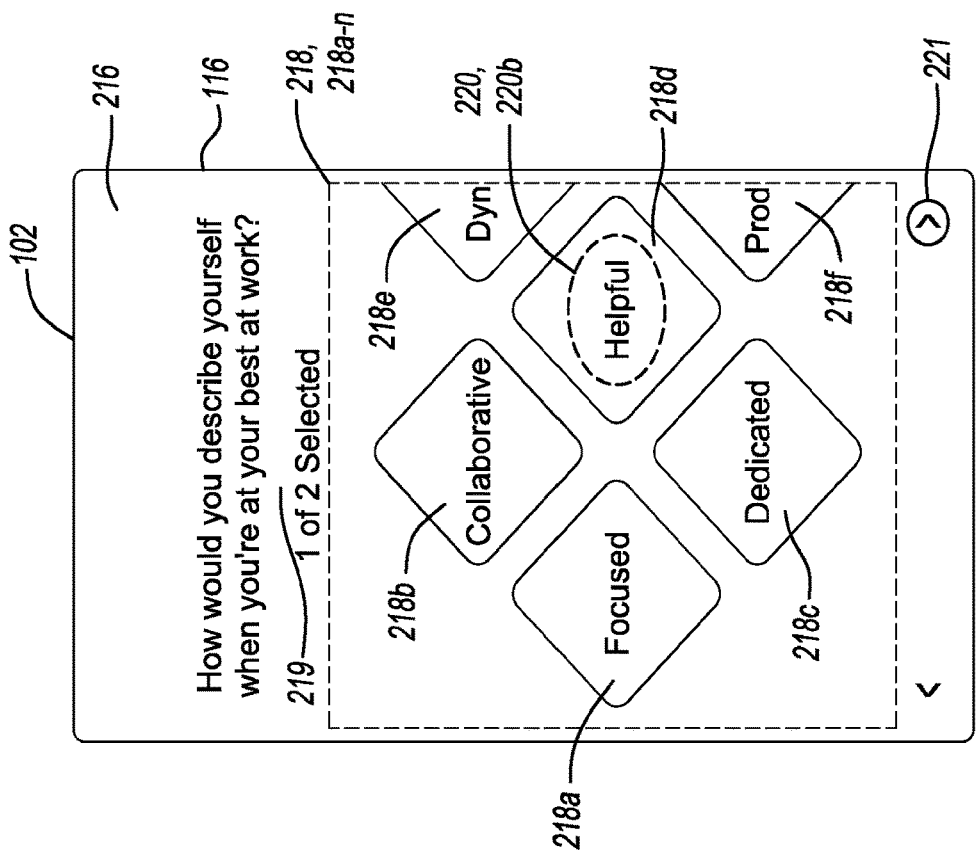
FIG. 2H illustrates another view of the work inquiry interface of FIG. 2F.
Figure 2G:
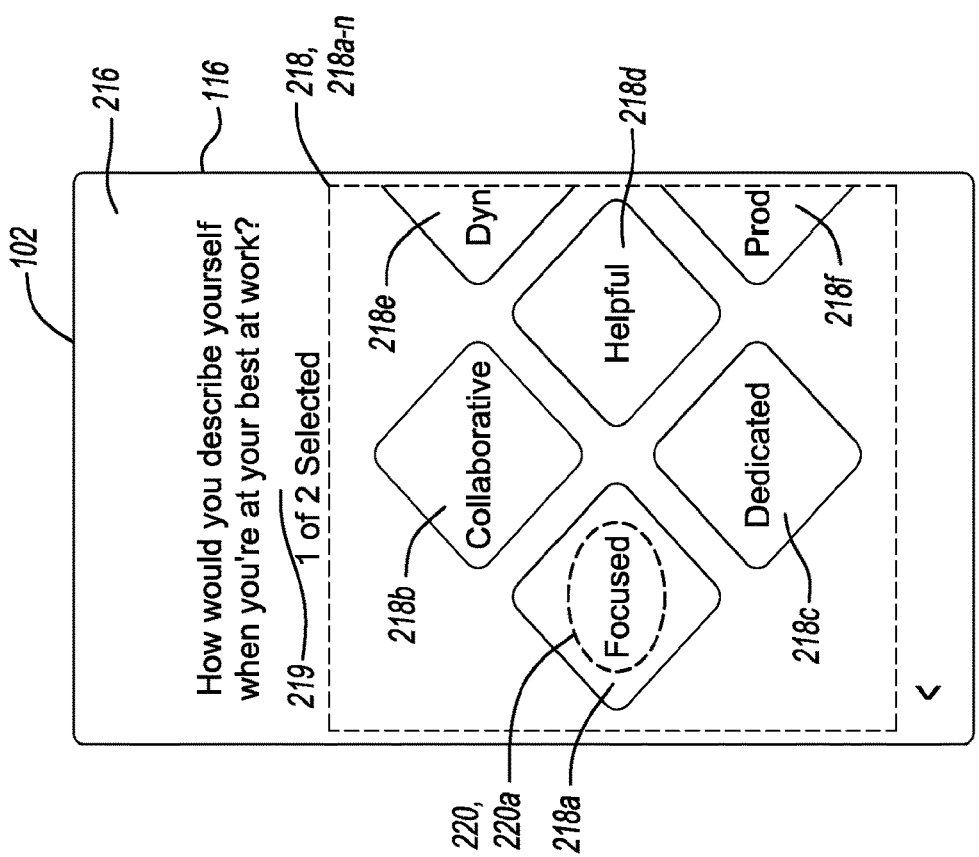
FIG. 2G illustrates another view of the work inquiry interface of FIG. 2F.

At FIGS. 2F-2H, in some configurations, the user application 103 causes the user device 102 to display the work inquiry GUI 216 that allows the user 101 to input a particular best trait they would use to describe themselves when they are at their best at work. In the example shown, GUI 216 allows the user 101 to select an input corresponding to traits that describe themselves when they are at their best at work. It should be noted that the inquiry work GUI 216 may inquire about a user's 101 traits in other settings, such as in church, at school, in support groups, and at home. Referring now to FIG. 2A, in the example shown, the work inquiry GUI 216 provides a plurality of selectable work inquiry interface elements 218 (e.g., buttons), each work inquiry interface element 218a-218n being associated with a corresponding trait at work that the user 101 may use to describe themselves when they are at their best at work. While the example shown depicts work inquiry interface elements 218a-218f, the user 101 may view additional interface elements 218n by scrolling (e.g., via a swipe gesture) on the display 116 of the user device 102. The work inquiry interface elements represent traits that an individual may use to describe themselves when they are at their best at work. Displaying work inquiry interface elements advantageously enables the user 101 to identify their behavior and align with their best self by allowing the user 101 to identify the traits they feel make them their best at work and reinforcing the idea that they should align with these traits in order to be their best.

With continued reference to FIG. 2F, in some embodiments, the plurality of work inquiry interface elements 218 may be prepopulated based on common traits that members of a general population believe to have when they are at their best at work. In other embodiments, the plurality of work inquiry interface elements 218 may be prepopulated based on common traits shared by a plurality of users 101, such as members of a sub-group or organization for which the digital purposeful behavior program 120 is intended to be used for. In some embodiments, the plurality of work inquiry interface elements 218 are randomized and displayed in a different order for each user 101. In other embodiments, the plurality of work inquiry interface elements 218 are generated based on information gathered on the user 101 and stored in data storage 158. For example, the plurality of work inquiry interface elements 218 may be generated and displayed for a particular user 101 using machine learning or artificial intelligence algorithms based on information gathered and stored in the data storage 158 for the particular user 101. In some implementations, the plurality of work inquiry interface elements 218 are generated based on information gathered and stored (e.g., in the data storage 158) on a group of which the user 101 is a member. For example, the plurality of work inquiry interface elements 218 may be generated using machine learning or artificial intelligence algorithms based on information gathered and stored in the data storage 158 for a group of users 101.

The work inquiry GUI 216 may provide instructions 219 ("How would you describe yourself when you're at your best at work?" and "Select 2"). Instructions 219 may prompt the user 101 to enter input corresponding to how the user 101 would describe themselves when they are at their best at work. Instructions 219 may also instruct the user 101 on how many work inquiry interface elements 218 to select. The user 101 may indicate a particular trait associated with them by selecting the corresponding work inquiry interface element 218 displayed in the work inquiry GUI 216. In the example shown, a first work inquiry interface element 218a ("Focused") indicates that the user 101 would describe themselves as focused when they are at their best at work. A second work inquiry interface element 218b ("Collaborative") indicates that the user 101 would describe themselves as collaborative when they are at their best at work. A third work inquiry interface element 218c ("Dedicated") indicates that the user 101 would describe themselves as dedicated when they are at their best at work. A fourth work inquiry interface element 218d ("Helpful") indicates that the user 101 would describe themselves as helpful when they are at their best at work. A fifth work inquiry interface element 218e ("Dynamic") (partially omitted from view) indicates that the user 101 would describe themselves as dynamic when they are at their best at work. A sixth work inquiry interface element 218f ("Productive") (partially omitted from view) indicates that the user 101 would describe themselves as productive when they are at their best at work.

Work inquiry interface elements 218a-218f do not represent an exhaustive list of all work inquiry interface elements, but rather an exemplary list of work inquiry interface elements that may be included on the work inquiry GUI 216. Furthermore, the work inquiry GUI 216 may include other work inquiry interface elements in addition to work inquiry interface elements 218a-218f, or may omit one or more work inquiry interface elements 218a-218f, without departing from the teachings herein.

Referring now to FIG. 2G, in the example shown, the user device 102 detects a work inquiry selection input 220 (e.g., touch or spoken) corresponding to a particular work inquiry interface element 218a-n. In some embodiments, the user device 102 detects only a single work inquiry selection input 220, corresponding to one work inquiry interface element. In other embodiments, the user device 102 detects more than one work inquiry selection input 220 corresponding to more than one work inquiry interface element. In the example shown, the user device 102 detects a first work inquiry selection input 220a corresponding to the work inquiry interface element 218a ("Focused") indicating the user 101 would describe themselves as focused when they are at their best at work. In some implementations, the first work inquiry selection input 220a causes the user application 103 to transmit time-stamped event data 122 to the purposeful behavior service 160 (FIG. 1) that includes a selection indication identifying that the user 101 believes they are at their best self at work when they are focused.

In some implementations, after detecting the first work inquiry selection input 220a, the user application 103 advances to display a work recap GUI 222 (FIG. 2I) on the display 116 of the user device 102. In other implementations, after detecting first work inquiry selection input 220a, the user application 103 indicates selection of the selected work inquiry interface element. For example, as illustrated in FIG. 2G, the user application 103 may change the display (e.g., highlight, change color, display check mark, or otherwise indicate selection of the element) of the selected work inquiry interface element(s) 218a-n (e.g., element 218a) on the display 116, while continuing to display the work inquiry GUI 216. The user application 103 may also displayed an updated version of instructions 219 displaying a message confirming the user 101 has made a selection (e.g., "1 of 2 selected").

Referring now to FIG. 2H, in the example shown, the user device 102 detects a second work inquiry selection input 220b corresponding to the work inquiry interface element 218d ("Helpful") indicating the user 101 would describe themselves as helpful when they are at their best at work. In some implementations, the second work inquiry selection input 220b causes the user application 103 to transmit time-stamped event data 122 to the purposeful behavior service 160 (FIG. 1) that includes a selection indication identifying that the user believes they are at their best self at work when they are helpful. The user application 103 may also displayed an updated version of instructions 219 displaying a message confirming the user 101 has made another selection (e.g., "2 of 2 selected").

In some examples, after detecting the second work inquiry selection input 220b, the user application 103 advances to the work recap GUI 222 (FIG. 2I) on the display 116 of the user device 102. In some configurations, detecting the second work inquiry selection input 220b causes the user application 103 to automatically display the work recap GUI 222. In other configurations, the user application 103 requires the user 101 to first confirm the selected work inquiry interface element 218 by selecting a confirmation element 221 (e.g., a button or arrow, as shown in FIG. 2H). In these configurations, the user application 103 displays the work recap GUI 222 in response to a selection indication identifying selection of the confirmation element 221.

Figure 2J:
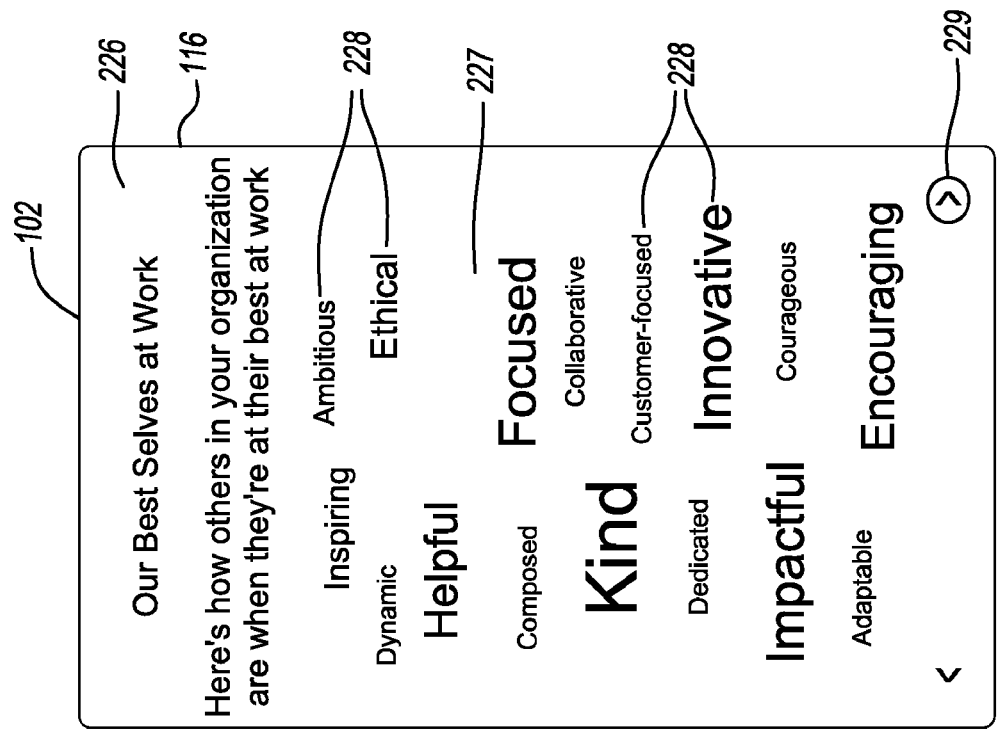
FIG. 2J illustrates a group work recap interface in accordance with the principles of the present disclosure.
Figure 2I:
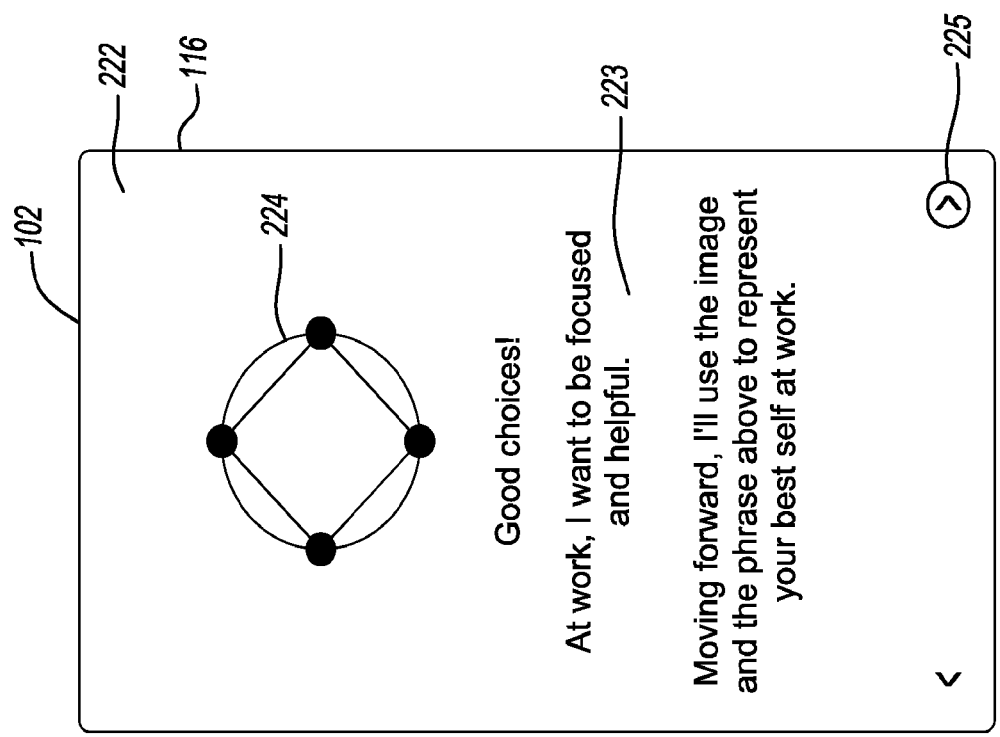
FIG. 2I illustrates a work recap interface in accordance with the principles of the present disclosure.

At FIG. 2I, in some configurations, the user application 103 causes the user device 102 to display the work recap GUI 222. Work recap GUI 222 may display a work constellation image 224. The work constellation image 224 may vary based on the selection by the user 101 in the work inquiry GUI 216 (FIG. 2F). In some configurations, the work constellation image 224 is randomized for each user 101. The display of the work constellation image 224 on the work recap GUI 222 is exemplary, as the work constellation image 224 may be present throughout any screen of the user application 103. The work recap GUI 222 may be beneficial for aligning the user 101 with their best traits at work by reinforcing and reminding the user of their selection in the work inquiry GUI 216. In particular, the work recap GUI 222 may include a displayed confirmation message 223 having one or more words or messages corresponding to the work inquiry interface elements 218*a-n*. For example, as illustrated in FIG. 2I, the confirmation message 223 may include the words "Focused" and "Helpful," corresponding to the work inquiry interface elements 218*a* and 218*d* selected in the work inquiry GUI 216.

In some configurations, the user application 103 requires the user 101 to select a confirmation element 225 (e.g., a button or arrow, as shown in FIG. 2I) in order for the user application 103 to advance to display a group work recap GUI 226 (FIG. 2J) on the display 116 of the user device 102. In other configurations, the user application 103 advances to display the group work recap GUI 226 on the display 116 of the user device 102 after a short period of time (e.g., 10 seconds) has passed.

At FIG. 2J, in some configurations, the user application 103 causes the user device 102 to display the group work recap GUI 226. The group work recap GUI 226 may present a plurality of best-self traits an individual may have at work that correspond to a particular group. The group may be populated based on a sub-group, geographic population, or the full user population. In the example shown the group work recap GUI 226 includes a displayed plurality of words 228 corresponding to work inquiry interface elements (e.g., work inquiry interface element 218*a-n*). In some implementations, the words 228 are represented by a word cloud, 227, where each word 228 in the word cloud 227 corresponds to a particular work trait an individual may have at work, and the size of each word 228 corresponds to a frequency that the word was selected by an individual in the group. For example, each word 228 in the word cloud 227 may correspond to a particular work trait selected by one or more individuals in the group (e.g., one or more users 101) at the work inquiry interface elements 218*a-n*, and the size of each word 228 may correspond to a frequency that the word 228 was selected by an individual in the group at the work inquiry interface elements 218*a-n*. Though FIG. 2J depicts a display with plurality of words 228 represented by a word cloud 227 to represent the plurality of best-self traits that an individual may have at work corresponding to a group, it should be noted that the plurality of best-self traits that an individual may have at work may be represented via stacked ranked lists, graphs, or other method of data visualization. FIG. 2J may display data corresponding to the user's 101 place of employment, a particular department with the user's 101 place of employment, or a particular region such as the country, state, or area in which the user 101 resides, enabling the user 101 to see how their best-self traits they may have at work align with multiple types of social groupings.

In some implementations, the plurality of words 228 is generated based on data stored in the data storage 158. In other implementations, the plurality of words 228 is generated using machine learning or artificial intelligence algorithms with data corresponding to data collected on the group using the application 103 and stored in the data storage 158. In yet other configurations, the plurality of words 228 is generated by data clustering or using typology to classify data in data storage 158 (e.g., classification based on purpose types). The plurality of words 228 may also be updated in real time.

In some implementations, the user application 103 requires the user 101 to select a confirmation element 229 (e.g., a button or arrow, as shown in FIG. 2J) in order for the user application 103 to advance to display a purposeful inquiry GUI 302 (FIG. 3A) on the display 116 of the user device 102. In other configurations, the user application 103 advances to the purposeful inquiry GUI 302 (FIG. 3A) on the display 116 of the user device 102 after a short period of time (e.g., 10 seconds) has passed.

Figure 3B:
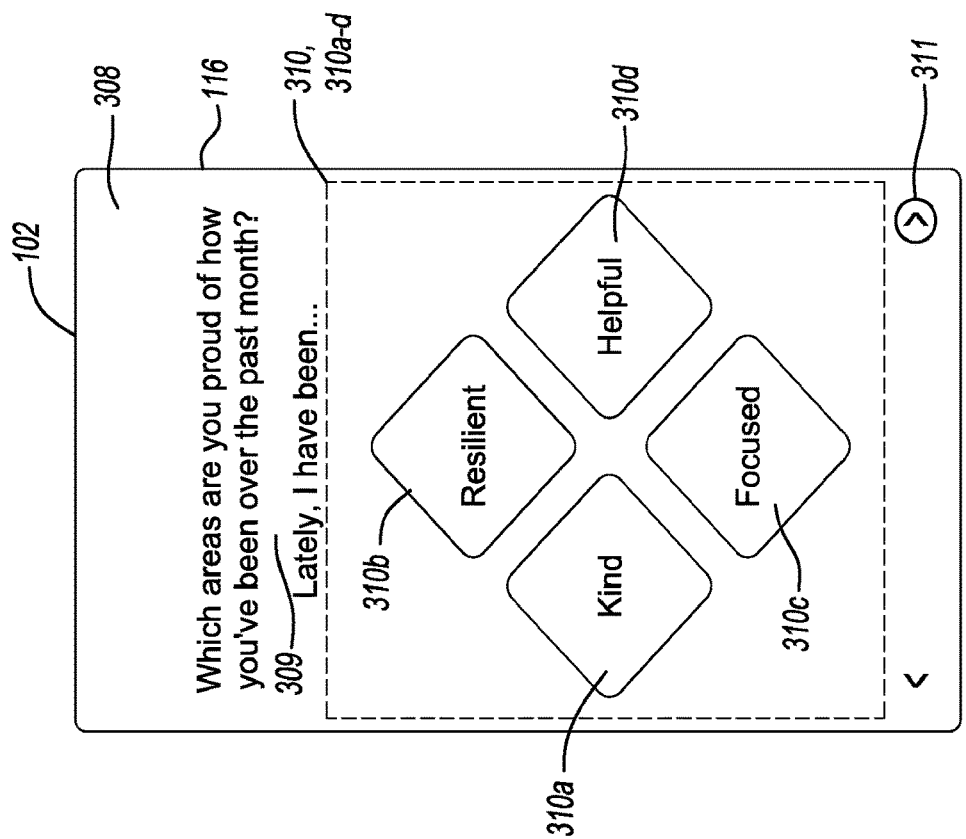
FIG. 3B illustrates a reflection inquiry interface in accordance with the principles of the present disclosure.
Figure 3A:
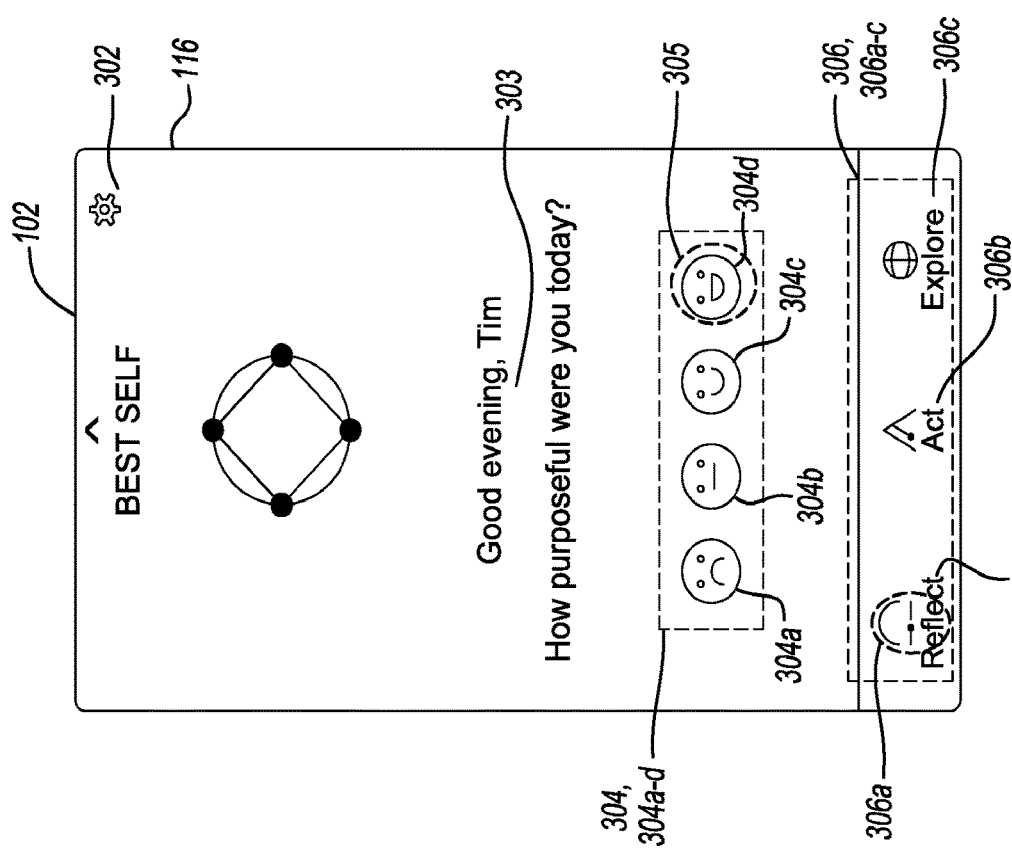
FIG. 3A illustrates a purposeful inquiry interface in accordance with the principles of the present disclosure.

At FIG. 3A, in some configurations, the user application 103 causes the user device 102 to display the purposeful inquiry GUI 302 that allows a user 101 to input a particular purposeful icon they would use to describe how purposeful they were that day.

In the example shown, GUI 302 allows the user 101 to select an input that corresponds with how purposeful they were that day by selecting one of the particular purposeful icons, represented by faces of varying emotion, to indicate how purposeful they were that day. The purposeful inquiry GUI 302 provides a plurality of selectable purposeful icon interface elements 304 (e.g., buttons), each purposeful icon interface element 304*a*-304*d* being associated with a corresponding level of purposeful that the user 101 may use to describe how purposeful they were that day. While the example shown depicts purposeful icon interface elements 304 as faces of varying emotions, it should be noted that the GUI 302 may provide for other means for the user 101 to enter in data corresponding to how purposeful they were that day, such as a sliding scale interface element or a free-text input to enter via words or numbers how purposeful the user 101 was that day. It should also be noted that, though in the example shown the GUI 302 asks the user 101 for information corresponding to how purposeful the user 101 was that day, in other implementations, the GUI 302 asks the user 101 about other best-traits in other settings, such as how resilient the user 101 was that day, or how focused the user 101 was that day or that week at work.

The purposeful inquiry GUI 302 may provide purposeful message 303 (e.g., "Good evening, Tim" and "How purposeful were you today?"). Purposeful message 303 may inquire about how purposeful the user 101 was that day. The user 101 may indicate how purposeful they were that day by selecting the corresponding purposeful icon interface element 304 displayed in the purposeful GUI 302. In the example shown, a first purposeful icon interface element 304*a* indicates that the user 101 did not have a purposeful day. A second purposeful icon interface element 304*b* indicates that the user 101 had a purposeful day to a degree of purposefulness more than the amount of purposefulness represented by purposeful icon interface element 304*a*. A third purposeful icon interface element 304*c* indicates that the user 101 had a purposeful day to a degree of purposefulness more than the amount of purposefulness represented by purposeful icon interface element 304*b*. A fourth purposeful icon interface element 304*d* indicates that the user 101 had a very purposeful day to a degree of purposefulness more than the amount of purposefulness represented by purposeful icon interface element 304*c*.

In some configurations, the user device 102 detects a purposeful selection input 305 (e.g., touch or spoken) corresponding to a particular purposeful icon interface element 304*a-d*. In the example shown, the user device 102 detects the purposeful selection input 305 corresponding to the fourth purposeful icon interface element 304*d*, indicating that the user 101 believes they had a very purposeful day. In some implementations, the purposeful selection input 305 causes the user application 103 to transmit time-stamped event data 122 to the purposeful behavior service 160 (FIG. 1) that includes a selection indication identifying that the user 101 believes they had a very purposeful day.

In some implementations, after detecting the purposeful selection input 305, the user application 103 advances to display the reflection inquiry GUI 308 (FIG. 3B) on the display 116 of the user device 102. In other implementations, after detecting the purposeful selection input 305, the user application 103 indicates selection of the selected purposeful icon interface element 304. For example, the user application 103 may change the display (e.g., highlight, change color, display check mark, or otherwise indicate selection of the element) of the selected purposeful icon interface element (e.g., element 304d) on the display 116, while continuing to display the GUI 302.

With continued reference to FIG. 3A, in some configurations, the purposeful inquiry GUI 302 presents a plurality of navigation elements 306, each navigation element 306a-306c corresponding to a particular GUI of the user application 103. Displaying navigation elements 306 allows a user to freely navigate through multiple GUIs of the user application 103. Each of the plurality of navigation elements 306 may correspond to a self-affirmation activity, such as a reflection activity, an educational activity, or a behavior identification or optimization activity. The display of the plurality of navigation elements 306 on the purposeful inquiry GUI 302 is exemplary, as the plurality of navigation elements 306 may be present throughout any screen of the user application 103. In the example shown, a first navigation element 306a ("Reflect") corresponds to a reflection inquiry GUI 308, a reflection improvement GUI 314, a reflection elaboration GUI 320, and a reflection completed GUI 324 (FIGS. 3B-3H). A second navigation element 306b ("Act") corresponds to an actions list GUI 328 and a habit inquiry GUI 332 (FIGS. 3I-3J). A third navigation element 306c ("Explore") corresponds to an explore GUI 340 (FIG. 3K).

In some implementations, the user device 102 detects a navigation selection input 307 (e.g., touch or spoken) corresponding to a particular navigation element 306a-c. In the example shown, the user device 102 detects the navigation selection input 307 corresponding to the navigation element 306a ("Reflect"), indicating that the user 101 would like to advance to the reflection inquiry GUI 308. In some implementations, the navigation selection input 307 causes the user application 103 to transmit time-stamped event data 122 to the purposeful behavior service 160 (FIG. 1) that includes a selection indication identifying that the user 101 wishes to advance to the reflection inquiry GUI 308. After detecting the navigation selection input 307, the user application 103 may advance to display the reflection inquiry GUI 308 (FIG. 3B) on the display 116 of the user device 102.

Figure 3D:
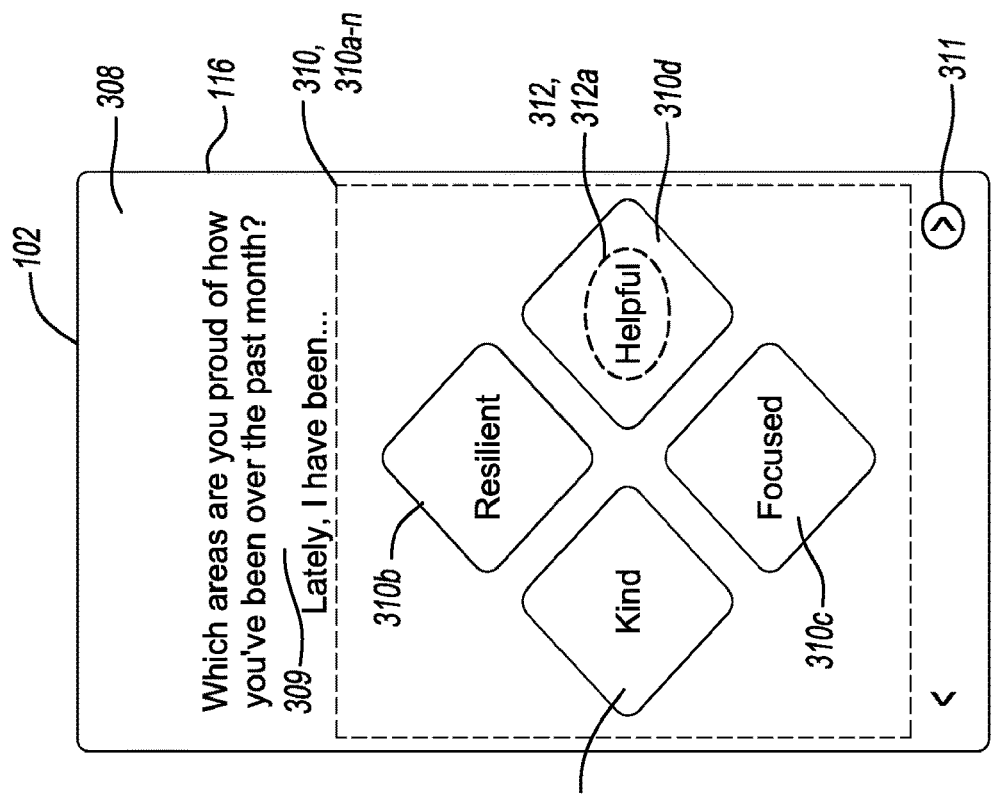
FIG. 3D illustrates another view of the reflection inquiry interface of FIG. 3B.
Figure 3C:
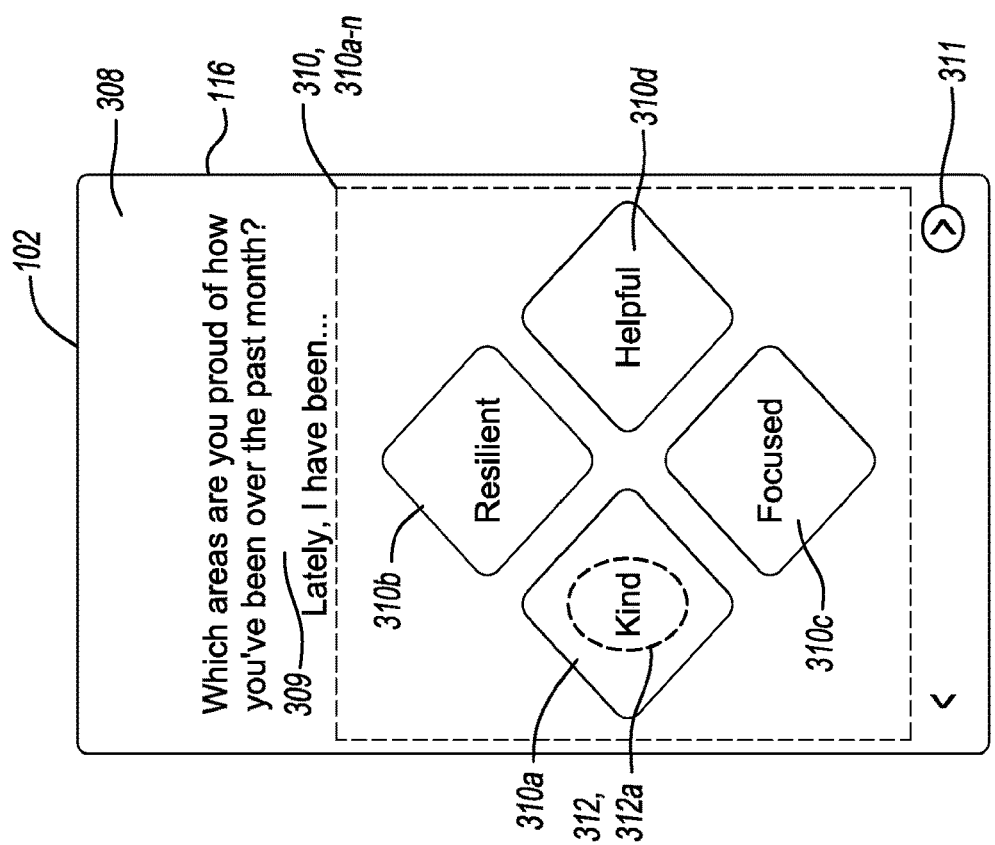
FIG. 3C illustrates another view of the reflection inquiry interface of FIG. 3B.

Referring to FIGS. 3B-3D, in some configurations, the user application 103 displays the reflection inquiry GUI 308 that allows the user 101 to input a particular best trait they feel proud of in the past month. In the example shown, the GUI 308 asks about the trait which the user identifies as being proud of in the past month, but it should be noted that GUI 308 can ask about areas or traits which the user 101 has identified as being proud of in the past hour, day, week, year, or any amount of time. GUI 308 may also not be limited to inquiring about the particular best trait which the user identified as being proud of. For example, the GUI 308 may also ask the user 101 other questions, such as what the user 101 has learned, or what the user 101 is grateful for. GUI 308 allows the user 101 to reflect on what areas they have been proud of how they have been over the past month.

Referring now to FIG. 3B, in the example shown, the reflection inquiry GUI 308 provides a plurality of selectable reflection interface elements 310 (e.g., buttons), each 310a-310d associated with a corresponding trait that the user 101 is proud of how their behavior has aligned with that trait over the past month. In some embodiments, the plurality of reflection interface elements 310 may be prepopulated based on common traits that members of a general population believe to be proud of in their lives. In other embodiments, the plurality of reflection interface elements 310 may be prepopulated based on common traits shared by a plurality of users 101, such as members of a sub-group or organization for which the digital purposeful behavior program 120 is intended to be used for. In some embodiments, the plurality of reflection interface elements 310 are randomized and displayed in a different order for each user 101. In other embodiments, the plurality of reflection interface elements 310 are generated based on information gathered on the user 101 and stored in data storage 158. For example, the plurality of reflection interface elements 310 may be generated and displayed for a particular user 101 using machine learning or artificial intelligence algorithms based on information gathered and stored in the data storage 158 for the particular user 101. In some implementations, the plurality of reflection interface elements 310 are generated based on information gathered and stored (e.g., in the data storage 158) on a group of which the user 101 is a member. For example, the plurality of reflection interface elements 310 may be generated using machine learning or artificial intelligence algorithms based on information gathered and stored in the data storage 158 for a group of users 101.

In some embodiments, the plurality of reflection interface elements 310 may correspond to the plurality of best-self inquiry interface elements 204 (FIGS. 2A-2C). In other embodiments, the plurality of reflection interface elements 310 may correspond to the plurality of work inquiry interface elements 218 (FIGS. 2F-2H). In yet other embodiments, the plurality of reflection interface elements 310 may correspond to the best-self inquiry selection input 206 (FIGS. 2B-2C) and the work inquiry selection input 220 (FIGS. 2G-2H).

The reflection inquiry GUI 308 may provide an inquiry message 309 (e.g., "Which areas are you proud of how you've been over the past month?" and "Lately I have been . . ."). Inquiry message 309 may prompt the user 101 to enter input corresponding to what areas the user 101 is proud of how they've been over the past month. The user 101 may indicate which areas they are proud of how they have been over the past month by selecting the corresponding reflection interface element 310 displayed in the reflection inquiry GUI 308. In the example shown, a first reflection interface element 310a ("Kind") indicates that the user 101 is proud of how kind they were for the past month. A second reflection interface element 310b ("Resilient") indicates that the user 101 is proud of how resilient they were for the past month. A third reflection interface element 310c ("Focused") indicates that the user 101 is proud of how focused they were for the past month. A fourth reflection interface element 310d ("Helpful") indicates that the user 101 is proud of how helpful they were for the past month.

The reflection interface elements 310a-310d do not represent an exhaustive list of all reflection interface elements, but rather an exemplary list of reflection interface elements that may be included as part of the reflection inquiry GUI 308. Furthermore, the reflection inquiry GUI 308 may include other reflection interface elements in addition to reflection interface elements 310a-310d, or may omit one or more reflection interface elements 310a-310d, without departing from the teachings herein.

Referring now to FIG. 3C, in the example shown, the user device 102 detects a reflection inquiry selection input 312 (e.g., touch or spoken) corresponding to a particular reflection interface element 310a-310d. In some embodiments, the user device 102 detects only a single reflection inquiry selection input 312, corresponding to one reflection interface element. In other embodiments, the user device 102 detects more than one reflection inquiry selection inputs 312 corresponding to more than one reflection interface elements. In the example shown, the user device 102 detects a first reflection inquiry selection input 312a corresponding to the reflection interface element 310a ("Kind") indicating the user 101 is proud of how kind they were for the past month. In some implementations, the first reflection inquiry selection input 312a causes the user application 103 to transmit time-stamped event data 122 to the purposeful behavior service 160 (FIG. 1) that includes a selection indication identifying that the user 101 is proud of how kind they were for the past month.

In some implementations, after detecting the first reflection inquiry selection input 312a, the user application 103 advances to display the reflection improvement GUI 314 on the display 116 of the user device 102. In other implementations, after detecting the first reflection inquiry selection input 312a, the user application 103 indicates selection of the selected reflection interface element 310. For example, as illustrated in FIG. 3C, the user application 103 may change the display (e.g., highlight, change color, display check mark, or otherwise indicate selection of the element) of the selected reflection interface element(s) 310a-d (e.g., element 310a) on the display 116, while continuing to display the reflection inquiry GUI 308.

Referring now to FIG. 3D, in the example shown, the user device 102 detects a second reflection inquiry selection input 312b corresponding to the reflection interface element 310d ("Helpful") indicating the user 101 is proud of how helpful they were for the past month. In some implementations, the second reflection inquiry selection input 312b causes the user application 103 to transmit time-stamped data 122 to the purposeful behavior service 160 (FIG. 1) that includes a selection indication identifying that the user 101 is proud of how helpful they were for the past month.

In some examples, after detecting the second reflection inquiry selection input 312b, the user application 103 advances to the reflection improvement GUI 314 (FIG. 3E) of the display 116 of the user device 102. In some configurations, detecting the second reflection inquiry selection input 312b causes the user application 103 to automatically display the reflection improvement GUI 314. In other configurations, the user application 103 requires the user 101 to first confirm the selected reflection interface element 310 by selecting a confirmation element 311 (e.g., a button or arrow, as shown in FIGS. 3B-3D). In these configurations, the user application 103 displays the reflection improvement GUI 314 in response to a selection indication identifying selection of the 311.

Figure 3F:
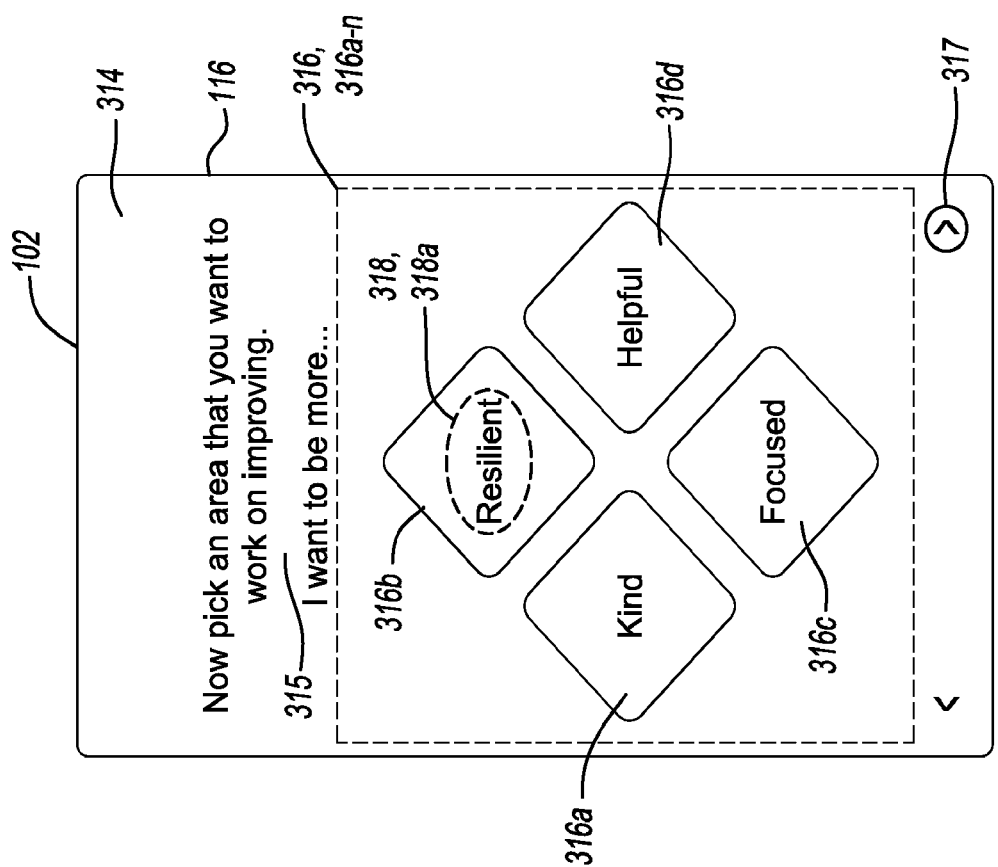
FIG. 3F illustrates another view of the reflection improvement interface of FIG. 3E.
Figure 3E:
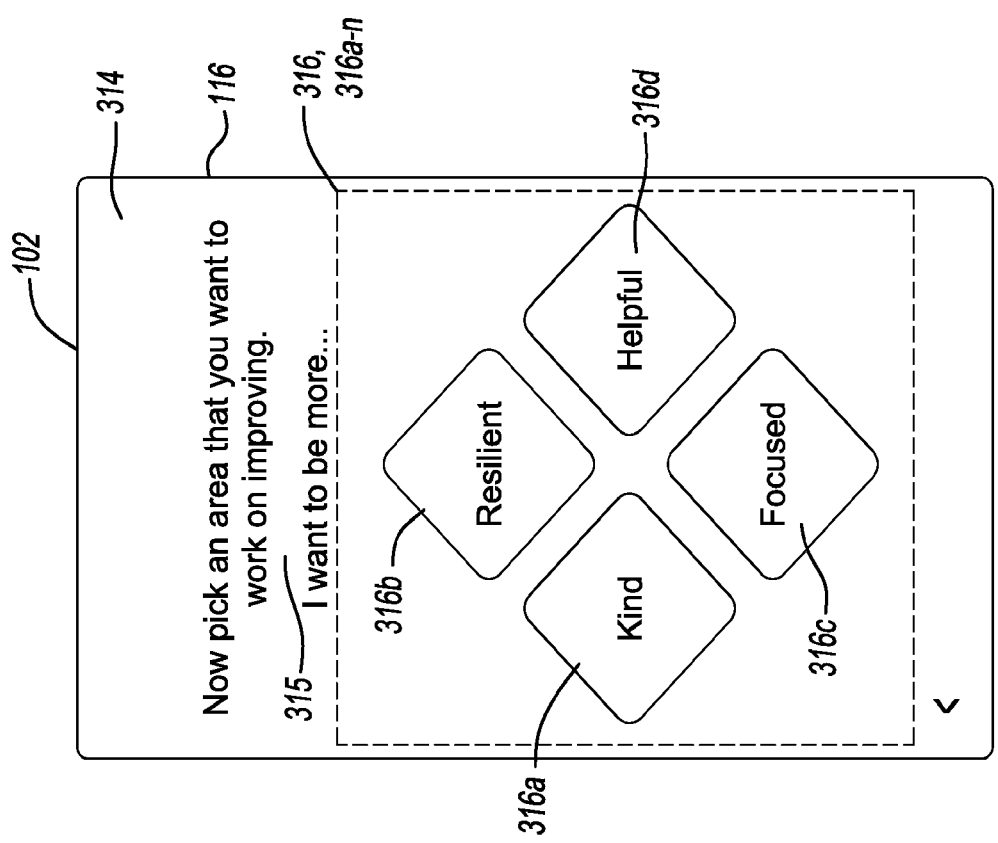
FIG. 3E illustrates a reflection improvement interface in accordance with the principles of the present disclosure.
Figure 3I:
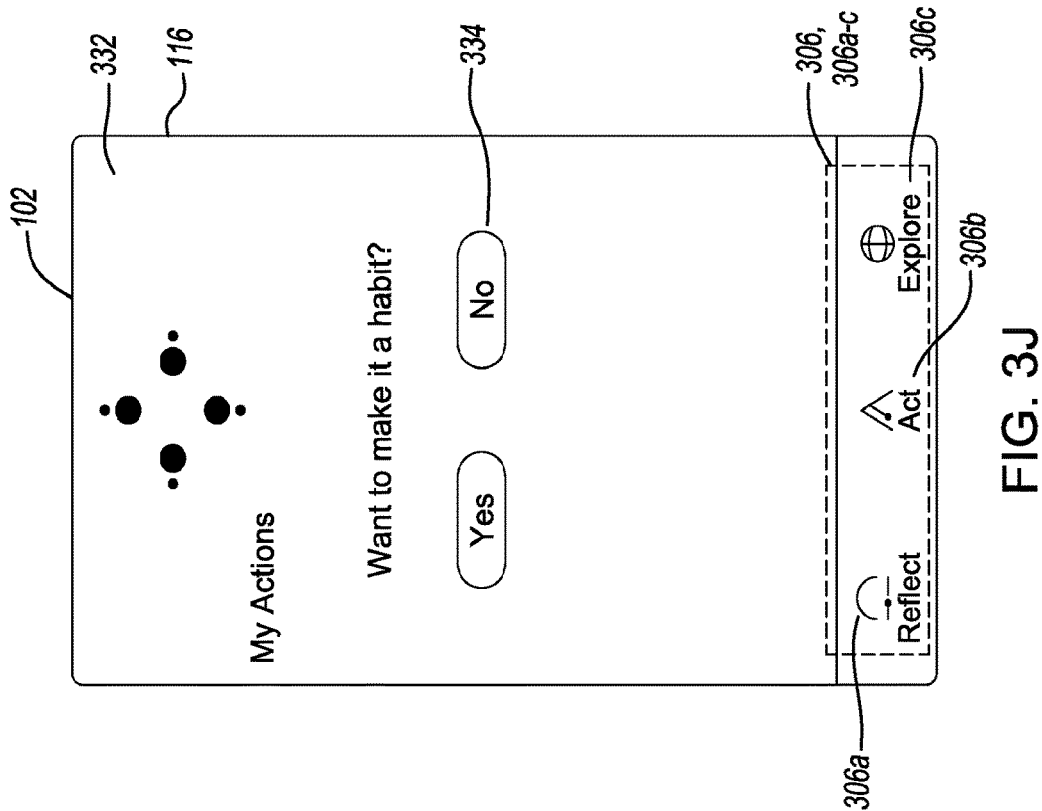
FIG. 3I illustrates an actions list interface in accordance with the principles of the present disclosure.
Figure 3J:
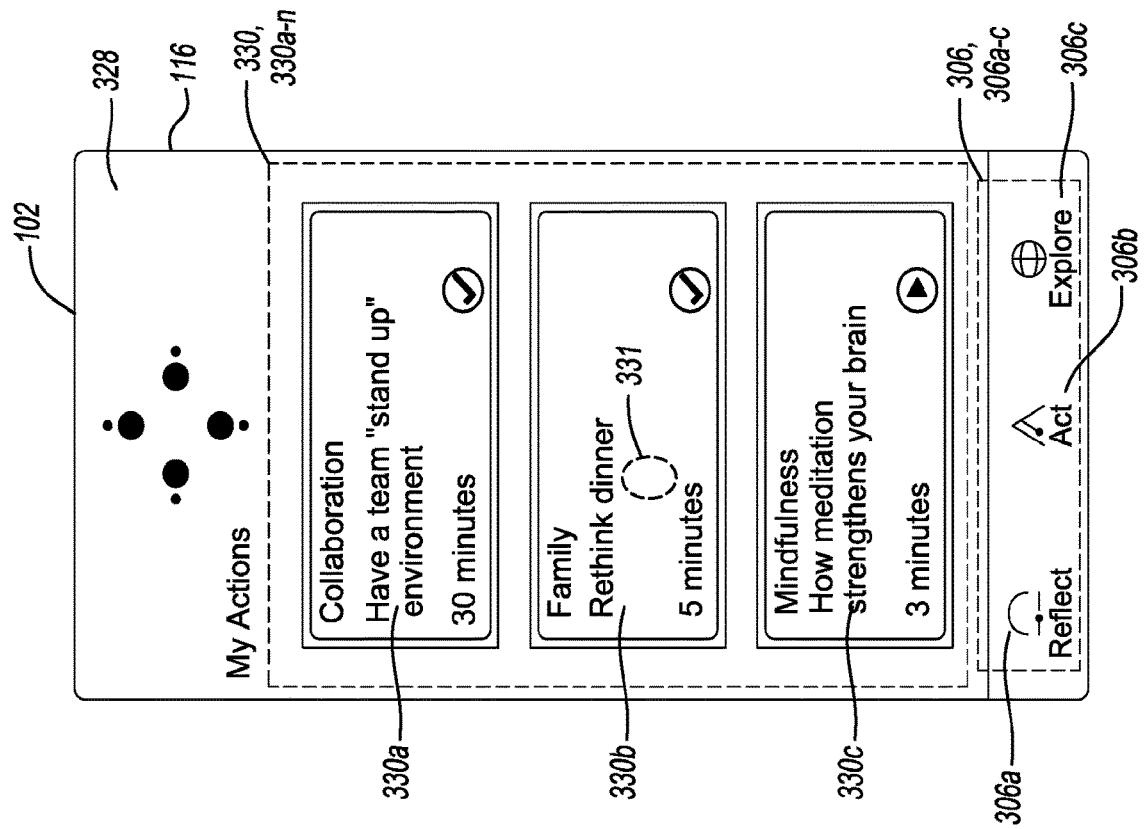
FIG. 3J illustrates an actions completed interface in accordance with the principles of the present disclosure.
Figure 3K:
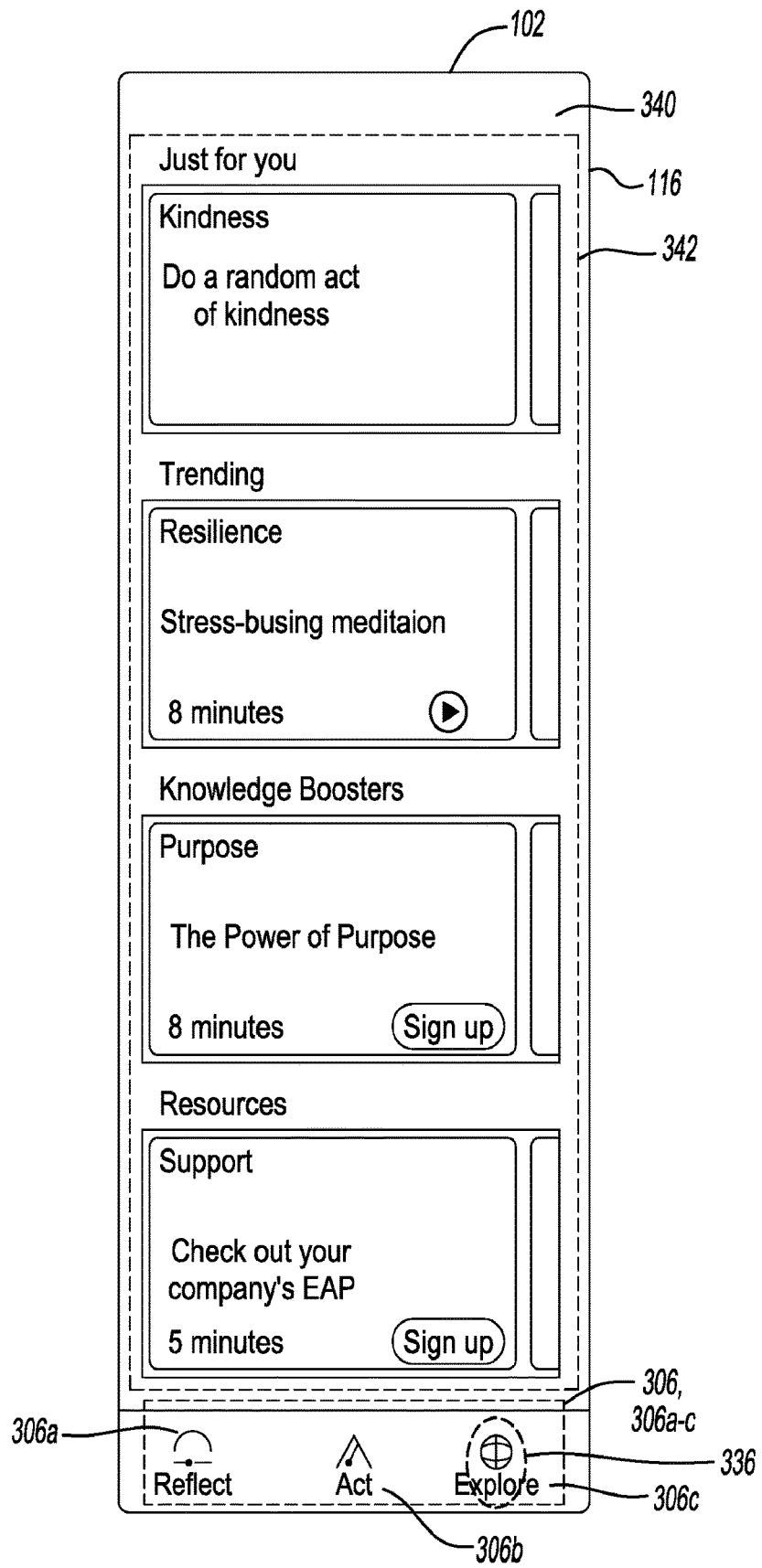
FIG. 3K illustrates an explore interface in accordance with the principles of the present disclosure.

Referring to FIGS. 3E-3F, in some configurations, the user application 103 displays the reflection improvement GUI 314 that allows the user 101 to input a particular trait they would want to work on improving. Referring now to FIG. 3E, in the example shown, the reflection improvement GUI 314 provides a plurality of selectable reflection improvement interface elements 316 (e.g., buttons), each 316a-d associated with a corresponding trait that the user 101 may wish to work on improving. In some embodiments, the plurality of reflection improvement interface elements 316 may be prepopulated based on common traits that members of a general population wish to work on improving. In other embodiments, the plurality of reflection improvement interface elements 316 may be prepopulated based on common traits shared by a plurality of users 101, such as members of a sub-group or organization for which the digital purposeful behavior program 120 is intended to be used for. In some embodiments, the plurality of reflection improvement interface elements 316 are randomized and displayed in a different order for each user 101. In other embodiments, the plurality of reflection improvement interface elements 316 are generated based on information gathered on the user 101 and stored in data storage 158. For example, the plurality of reflection improvement interface elements 316 may be generated and displayed for a particular user 101 using machine learning or artificial intelligence algorithms based on information gathered and stored in the data storage 158 for the particular user 101. In some implementations, the plurality of reflection improvement interface elements 316 are generated based on information gathered and stored (e.g., in the data storage 158) on a group of which the user 101 is a member. For example, the plurality of reflection improvement interface elements 316 may be generated using machine learning or artificial intelligence algorithms based on information gathered and stored in the data storage 158 for a group of users 101.

In some embodiments, the plurality of reflection improvement interface elements 316 may correspond to the plurality of best-self inquiry interface elements 204 (FIGS. 2A-2C). In other embodiments, the plurality of reflection improvement interface elements 316 may correspond to the plurality of work inquiry interface elements 218 (FIGS. 2F-2H). In yet other embodiments, the plurality of reflection improvement interface elements 316 may correspond to the best-self inquiry selection input 206 (FIGS. 2B-2C) and the work inquiry selection input 220 (FIGS. 2G-2H).

The reflection improvement GUI 314 may provide an instruction 315 (e.g., "Now pick an area that you want to work on improving?" and "I want to be more . . . "). Instruction 315 may prompt the user 101 to enter input corresponding to an area they want to work on improving. The user 101 may indicate an area that they want to work on improving by selecting the corresponding reflection improvement interface element 316 displayed in the reflection improvement GUI 314. Allowing the user 101 to identify and select traits they would like to improve on is advantageous in enabling a user to identify their behavior to align with their best self. In the example shown, a first reflection improvement interface element 316a ("Kind") indicates that the user 101 would like to improve on being more kind. A second reflection improvement interface element 316b ("Resilient") indicates that the user 101 would like to improve on being more resilient. A third reflection improvement interface element 316c ("Focused") indicates that the user 101 would like to improve on being more focused. A fourth reflection improvement interface element 316d ("Helpful") indicates that the user 101 would like to improve on being more helpful.

The reflection improvement interface elements 316a-316d do not represent an exhaustive list of all reflection improvement interface elements, but rather an exemplary list of reflection improvement interface elements that may be included as part of the reflection improvement GUI 314. Furthermore, the reflection improvement GUI 314 may include other reflection improvement interface elements in addition to reflection improvement interface elements 316a-316d, or may omit one or more reflection improvement interface elements 316a-316d, without departing from the teachings herein.

Referring now to FIG. 3F, in the example shown, the user device 102 detects a reflection improvement selection input 318 (e.g., touch or spoken) corresponding to a particular reflection improvement interface element 316a-d. In some embodiments, the user device 102 detects only a single reflection improvement selection input 318, corresponding to only one reflection improvement interface element. In other embodiments, the user device 102 detects more than one reflection improvement selection inputs 318 corresponding to more than one reflection improvement interface elements. In the example shown, the user device 102 detects a first reflection improvement selection input 318*a* corresponding to the reflection improvement interface element 316*b* ("Resilient") indicating that the user 101 would like to improve on being more resilient. In some implementations, the first reflection improvement selection input 318*a* causes the user application 103 to transmit time-stamped event data 122 to the purposeful behavior service 160 (FIG. 1) that includes a selection indication identifying that the user 101 would like to improve on being more resilient.

In some implementations, after detecting the first reflection improvement selection input 318*a*, the user application 103 advances to display the reflection elaboration GUI 320 (FIG. 3G) on the display 116 of the user device 102. In other implementations, after detecting the first reflection improvement selection input 318*a*, the user application 103 indicates selection of the selected reflection improvement interface element. For example, as illustrated in FIG. 3F, the user application 103 may change the display (e.g., highlight, change color, display check mark, or otherwise indicate selection of the element) of the selected reflection improvement element(s) 318*a-d* (e.g., element 318*a*) on the display 116, while continuing to display the GUI 314. In other configurations, the user application 103 requires the user 101 to first confirm the selected reflection improvement interface element by selecting a confirmation element 317 (e.g., a button or arrow, as shown in FIG. 3F). In these configurations, the user application 103 displays the reflection elaboration GUI 320 in response to a selection indication identifying selection of the confirmation element 317.

At FIG. 3G, in some configurations, the user application 103 causes the user device 102 to display the reflection elaboration GUI 320. The reflection elaboration GUI 320 may display free-form text input 322 that allows the user 101 to insert free text corresponding to why working on a particular best trait is important to them. In some implementations, the user application 103 may use natural language processing to process a user's free text input through artificial intelligence to generate application content. For example, through artificial intelligence, the user application 103 may utilize natural language processing on a user's free text input in order to select future reflections or to generate content in the application. The user 101 inputting free text corresponding to why it is important that they work on a particular trait is advantageous in identifying the user's 101 behavior because it facilitates the user's 101 self-reflection by having the user 101 describe why working on a particular trait is advantageous. This helps facilitate the user 101 to align with that trait by helping the user 101 realize why aligning with that trait is important. In the example shown, the reflection elaboration GUI 320 asks the user 101 why aligning with a particular trait is important to him or her, however it should be noted that the reflection elaboration GUI 320 can make other inquiries that allow the user 101 to reflect on what traits are important to them and further help the user 101 align with their best self. In some implementations, the user application 103 may utilize yes/no questions, radio button questions, slider questions, checklist questions, etc., in lieu of or in addition to free form text input, to allow the user 101 to input why working on a particular best trait is important to them.

With continued reference to FIG. 3G, the reflection elaboration GUI 320 may provide an inquiry message 321 (e.g., "Okay.", "So we'll start by working on that." and "Why is it important to you?"). Inquiry message 321 may prompt the user 101 to enter input corresponding why it is so important to them. In the example shown, the user 101 has inputted text input 322 ("I want to handle stress better.") indicating that the user 101 wants to handle stress better. In some implementations, the text input 322 causes the user application 103 to transmit time-stamped event data 122 to the purposeful behavior service 160 (FIG. 1) that includes a selection indication identifying that the user 101 wants to handle stress better.

In some configurations, the user application 103 requires the user 101 to select a confirmation element 323 (e.g., a button or arrow, as shown in FIG. 3G) in order for the user application 103 to advance to display the reflection completed GUI 324 (FIG. 3H) on the display 116 of the user device 102. In other configurations, the user application 103 advances to display the reflection completed GUI 324 on the display 116 of the user device 102 after a short period of time (e.g., 10 seconds) has passed.

At FIG. 3H, in some implementations, the user application 103 causes the user device 102 to display the reflection completed GUI 324. The reflection completed GUI 324 may display a confirmation message 325, indicating that the user 101 has completed their reflection. The confirmation message 325 may further include a message encouraging the user 101 to engage in other activities (e.g., follow-up reflections). These other activities may be activities that allow the user 101 to identify their behavior and align themselves with their best traits. The reflection completed GUI 324 may further display a plurality of suggested activity interface elements 326, each suggested activity interface element 326*a*-326*n* corresponding to a particular activity that allows the user 101 to identify their behavior and align with their best self. While the example shown depicts suggested activity interface elements 326*a*-326*b*, the user 101 may view additional interface elements 326*n* by scrolling (e.g., via a swipe gesture) on the display 116 of the user device 102. The suggested activity interface elements 326*n* include activities that the user 101 can engage in to align with their best self or to identify their behavior. In the example shown, a first suggested activity interface element 326*a* ("Reflect on your work environment") suggests that the user 101 should consider engaging in the activity of reflecting on their work environment. A second suggested activity interface element 326*b* ("Help others around you") suggests that the user 101 should consider engaging the in the activity of helping others around them.

With continued reference to FIG. 3H, in some embodiments, the plurality of suggested activity interface elements 326 may be prepopulated based on common activities that members of a general population engage in in order to align themselves with their best self. In other embodiments, the plurality of work inquiry interface elements 218 may be prepopulated based on common activities engaged in by members of the sub-group or organization for which the digital purposeful behavior program 120 is intended to be used for.

Suggested activity interface elements 326 do not represent an exhaustive list of all suggested activity interface elements, but rather an exemplary list of suggested activity interface elements that may be included on the reflection completed GUI 324. Furthermore, the reflection completed GUI 324 may include other suggested activity interface elements in addition to suggested activity interface elements 326a-326b, or may omit one or more suggested activity interface elements 326a-326b, without departing from the teachings herein. In the example shown, the user device 102 detects an act input 327 (e.g., touch or spoken) corresponding to the second navigation element 306b ("Act"), which may cause the user device 102 to display the actions list GUI 328.

Referring now to FIG. 3I, in some configurations, the user application 103 causes the user device 102 to display the actions list GUI 328. The actions list GUI 328 may present a plurality of actions list activities each corresponding to a particular action or activity that will allow the user 101 to engage in and identify their behavior to align with their best self. In the example shown, the actions list GUI 328 presents a plurality of actions list interface elements 330, each actions list interface element 330a-330n being associated with a corresponding activity that allows the user 101 to align with his or her best self. While the example shown depicts actions list interface elements 330a-330c, the user 101 may view additional interface elements 330n by scrolling (e.g., via a swipe gesture) on the display 116 of the user device 102. The actions list interface elements represent activities or actions that, if performed or completed by the user 101, will identify their behavior and allow them to align with their best self. Displaying actions list interface elements advantageously informs the user 101 what particular activities or actions they could perform or complete in order to identify their behavior and align with their best self by allowing the user 101 to identify the action or activity they wish to partake in and reinforcing the idea that the user 101 should perform these actions or complete these activities in order to align with their best self.

With continued reference to FIG. 3I, in some embodiments, the plurality of actions list interface elements 330 may be prepopulated based on common activities or actions that members of the general population engage in or complete in order to align with their best selves. In other embodiments, the plurality of actions list interface elements 330 may be prepopulated based on common activities engaged in by members of the sub-group or organization for which the digital purposeful behavior program 120 is intended to be used for. The user 101 may navigate through the actions list GUI 328 and explore different actions list interface elements 330 in order to learn about and select activities that the user 101 wishes to partake in in order to align with their best self. In the example shown, a first actions list interface element 330a ("Have a team 'stand up'") suggests that the user 101 could have a team "stand up." A second actions list interface element 330b ("Rethink dinner") suggests that the user 101 could rethink dinner. A third actions list interface element 330c ("How meditation strengths your brain") suggests that the user 101 could read about how meditation strengthens their brain. Actions list interface elements 330a-n may include text, audio, video, images, or links to external content.

Actions list interface elements 330a-330c do not represent an exhaustive list of all actions list interface elements, but rather an exemplary list of actions list interface elements that may be included on the actions list GUI 328. Furthermore, the actions list GUI 328 may include other actions list interface elements in addition to actions list interface elements 330a-330c, or may omit one or more actions list interface elements 330a-330c, without departing from the teachings herein. In some embodiments, the user device 102 detects an actions list input 331 (e.g., touch or spoken) corresponding to a particular actions list interface element 330a-c. In the example shown, the user device 102 detects the actions list input 331 corresponding to the second actions list interface element 330b ("Rethink dinner") indicating that the user 101 has selected the suggestion to rethink dinner. In some implementations, the actions list input 331 causes the user application 103 to transmit time-stamped event data 122 to the purposeful behavior service 160 (FIG. 1) that includes a selection indication identifying that the user 101 has selected the suggestion to rethink dinner.

At FIG. 3J, in some implementations, after detecting the actions list input 331, the user application 103 advances to display the habit inquiry GUI 332 on the display 116 of the user device 102. The habit inquiry GUI 332 may display a habit inquiry interface element 334, asking the user 101 whether they would like to make the actions list interface element that corresponds to the actions list input 331 a habit. Upon selecting "Yes," the user 101 may cause the user application 103 to save the actions list interface element that corresponds to the actions list input 331 to remain present in the actions list GUI 328 (FIG. 3I). Upon selecting "No," the user 101 may cause the application 103 to remove the actions list interface element that corresponds to the actions list input 331 from the actions list GUI 328. In some implementations, the user device 102 detects an explore input 336, causing the user application 103 to advance to the explore GUI 340 (FIG. 3K).

At FIG. 3K, in some configurations, the user application 103 causes the user device 102 to display the explore GUI 340. Explore GUI 340 may display a list of explore interface elements 342, which may include various activities, tips, recommendations, and resources. The list of explore interface elements 342 is advantageous to enabling the user 101 to align with their best self by providing the user 101 with various activities, tips, recommendations, resources, and other related types of information that will improve or optimize the behavior of user 101. In some embodiments, the list of explore interface elements 342 is prepopulated based on common activities, tips, recommendations, and resources that members of a general population use in their lives. In other embodiments, the list of explore interface elements 342 may be prepopulated based on common activities, tips, recommendations, and resources shared by a plurality of users 101, such as members of a sub-group or organization for which the digital purposeful behavior program 120 is intended to be used for. For example, the list of explore interface elements 342 may be generated based on data in the data storage 158, such as characteristic data of an individual user 101 or a plurality of users 101. In some embodiments, the list of explore interface elements 342 is generated based on machine learning and artificial intelligence algorithms using data corresponding to the user 101 from data storage 158. In other embodiments, the list of explore interface elements 342 is generated based on machine learning and artificial intelligence algorithms using data corresponding to a group that the user 101 is a member of, the data being stored in data storage 158.

FIG. 4 is a flow chart illustrating a method 400 for identification of purposeful behavior in accordance with an example implementation of the disclosed technology. According to one example, the method 400 may be performed by an electronic device, such as the user device 102. The method 400 begins at block 402 where the electronic device displays a purposeful inquiry interface (e.g., the explore GUI 340). The purposeful inquiry interface may include a plurality of navigation elements (e.g., selectable interface elements 342). Each of the plurality of navigation elements may correspond to a self-affirmation activity. The plurality of navigation elements may include a first navigation element corresponding to an explore interface.

At block 404, the method includes receiving, at the electronic device, a first navigation selection input. For example, the electronic device may receive the first navigation selection input from the user 101. In some implementations, the electronic device receives the first navigation selection input while displaying the purposeful inquiry interface. The first navigation selection input may correspond to the first navigation element.

At block 406, the method may include displaying the explore interface on the electronic device. In some implementations, the electronic device displays the explore interface at block 406 in response to receiving the first navigation selection input at block 404. The explore interface may include a plurality of explore interface elements. Each explore interface element may correspond to a particular activity.

At block 408, the method may include receiving, at the electronic device, one or more explore selection inputs. In some implementations, the electronic device receives the one or more explore selection inputs while displaying the explore interface. The one or more explore selection inputs may correspond to a particular explore interface element.

At block 410, the method may include storing, at the electronic device, data associated with the one or more explore selection inputs. In some implementations, the electronic device stores the data associated with the one or more explore selection inputs in response to receiving the one or more explore selection inputs. The electronic device may store the data in at least one database. Following block 410, the method 400 may conclude.

Figure 5:
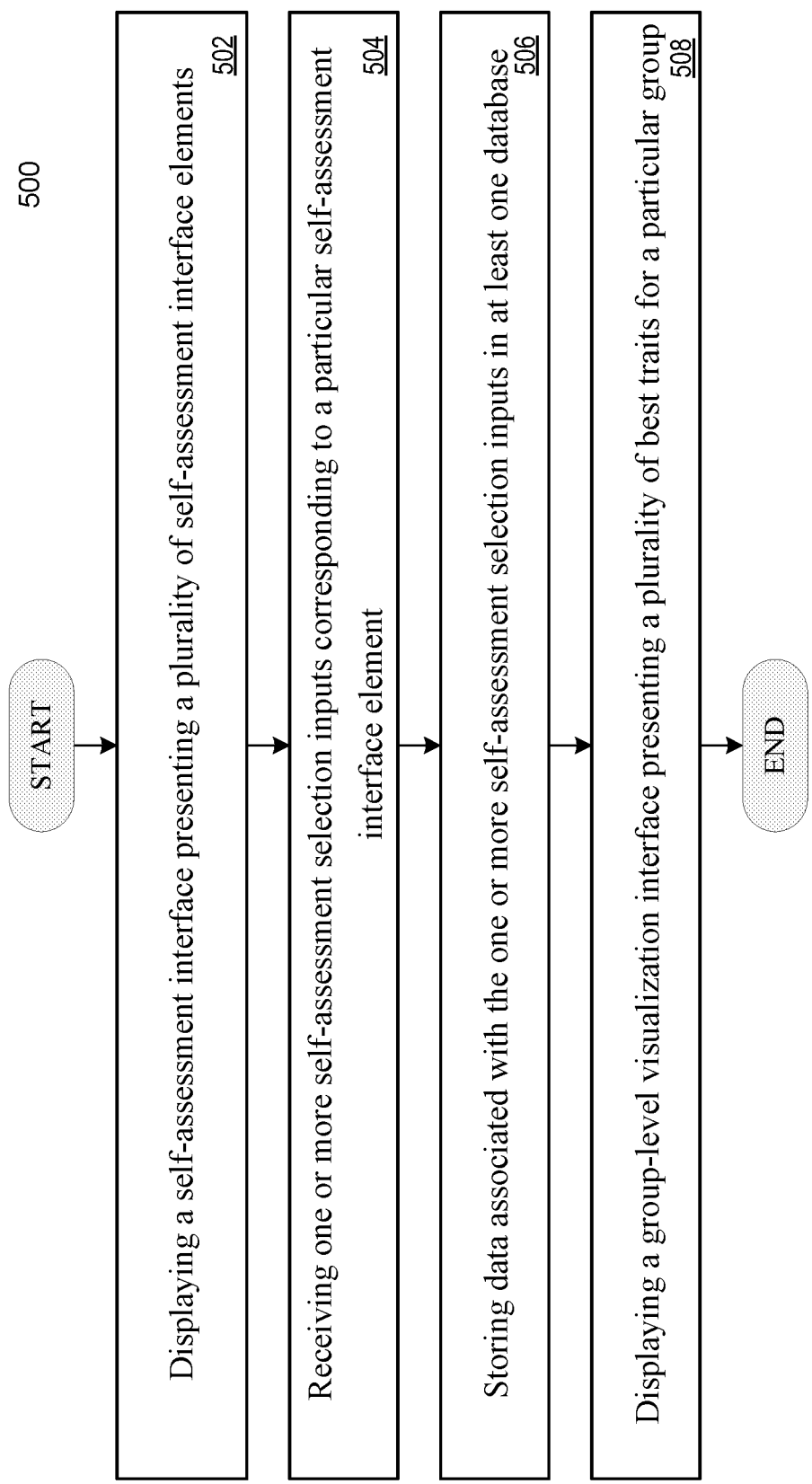
FIG. 5 is a flowchart illustrating another computerized method for identification of purposeful behavior in accordance with an exemplary embodiment of the disclosure.

FIG. 5 is a flow chart illustrating another method 500 for identification of purposeful behavior in accordance with an example implementation of the disclosed technology. According to one example, the method 500 may be performed by an electronic device, such as the user device 102. The method 500 begins at block 502 where the electronic device displays a self-assessment interface (e.g., the reflection inquiry GUI 308). The self-assessment interface may include a plurality of self-assessment interface elements (e.g., the selectable interface elements 310). Each of the plurality of self-assessment interface elements may correspond to a best trait. At block 504, the method includes receiving, at the electronic device, one or more self-assessment selection inputs. For example, the electronic device may receive the reflection inquiry selection input from the user 101. In some implementations, the electronic device receives the reflection inquiry selection input while displaying the self-assessment interface. The one or more self-assessment selection inputs may correspond to a particular self-assessment interface element.

At block 506, the method may include storing, at the electronic device, data associated with the one or more self-assessment selection inputs. In some implementations, the electronic device stores the data associated with the one or more self-assessment selection inputs in response to receiving the one or more self-assessment selection inputs. The electronic device may store the data in at least one database. At block 508, the electronic device displays a group-level visualization interface. The group-level visualization interface includes a plurality of best traits for a particular group. Following block 508, the method 500 may conclude.

Figure 6:
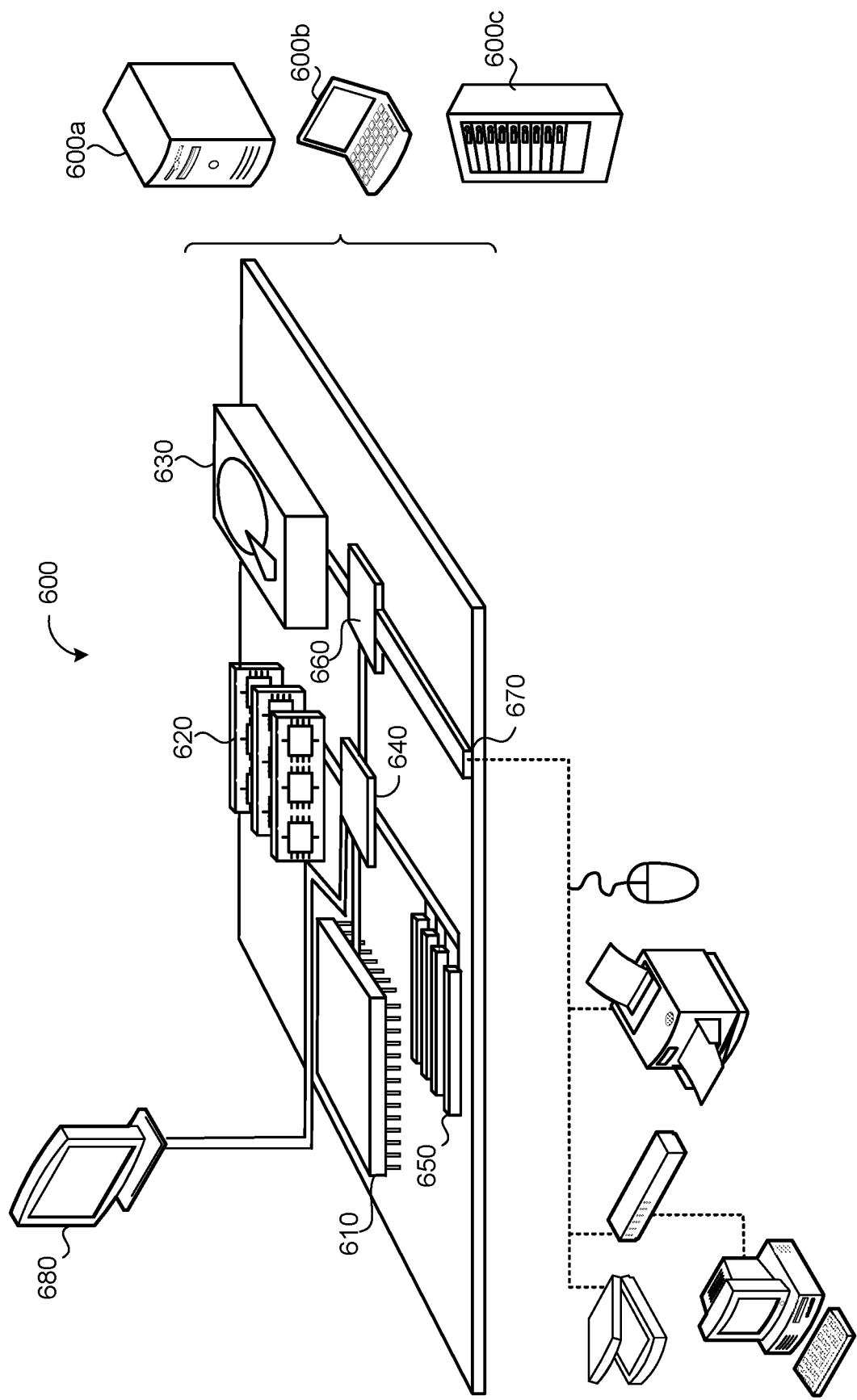
FIG. 6 is a schematic view of an example computing device that may be used to implement the systems and methods described herein.

FIG. 6 is schematic view of an example computing device 600 that may be used to implement the systems and methods described in this document. The computing device 600 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 600 includes a processor 610, memory 620, a storage device 630, a high-speed interface/controller 640 connecting to the memory 620 and high-speed expansion ports 650, and a low speed interface/controller 660 connecting to a low speed bus 670 and a storage device 630. Each of the components 610, 620, 630, 640, 650, and 660, are interconnected using various busses, and may be mounted on a common motherboard or in other manners as appropriate. The processor 610 can process instructions for execution within the computing device 600, including instructions stored in the memory 620 or on the storage device 630 to display graphical information for a graphical user interface (GUI) on an external input/output device, such as display 680 coupled to high speed interface 640. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 620 stores information non-transitorily within the computing device 600. The memory 620 may be a computer-readable medium, a volatile memory unit(s), or non-volatile memory unit(s). The non-transitory memory 620 may be physical devices used to store programs (e.g., sequences of instructions) or data (e.g., program state information) on a temporary or permanent basis for use by the computing device 600. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 630 is capable of providing mass storage for the computing device 600. In some implementations, the storage device 630 is a computer-readable medium. In various different implementations, the storage device 630 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 620, the storage device 630, or memory on processor 610.

The high speed controller 640 manages bandwidth-intensive operations for the computing device 600, while the low speed controller 660 manages lower bandwidth-intensive operations. Such allocation of duties is exemplary only. In some implementations, the high-speed controller 640 is coupled to the memory 620, the display 680 (e.g., through a graphics processor or accelerator), and to the high-speed expansion ports 650, which may accept various expansion cards (not shown).

The computing device 600 may be implemented in a number of different forms, as shown in the figure. For example, it may be implemented as a standard server 600a or multiple times in a group of such servers 600a, as a laptop computer 600b, or as part of a rack server system 600c.

Among other advantages, the present disclosure provides electronic devices and methods for helping a user align with their best-self traits and purpose through self-affirmation and data visualization, daily or periodic reflection, and/or curated and artificial intelligence/machine learning driven trips (recommendations).

The present disclosure also provides electronic devices and methods for an automated self-affirmation process that captures best-self traits (characteristics), builds an individual data visualization in real-time, and builds a group data visualization (purpose graph) in real time.

The present disclosure also provides electronic devices and methods for a daily purposeful best-self reflection process that captures purpose alignment as well as best-self trait alignment, charts alignment visually over time, and informs dynamic recommendations.

The present disclosure also provides electronic devices and methods for a recommendations engine that incorporates self-affirmation/purpose data to make artificial intelligence driven suggestions or lessons from among a set of options, incorporates custom content (suggestions or lessons) from sponsors and users, and utilizes machine learning to refine purposeful suggestions over time based on user attributes and content performance.

The present disclosure also provides electronic devices and methods for an analytics engine that surveils group-level data on purpose and best-self alignment to provide group and sub-group level data visualization, deliver artificial intelligence driven insights and decision support, track purpose alignment for organizations, and show relationship with defined business outcomes.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some implementations of the disclosed technology.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

Various implementations of the electronic devices, systems, techniques, and modules described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage resource, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method comprising:
   storing, at a memory in communication with data processing hardware, at least one database comprising a group-level dataset for a plurality of members of a particular group that includes a particular user, the group-level dataset for the particular group comprising corresponding current best traits for each particular member of the plurality of members of the particular group that the particular member has self-identified as their current best traits;
   generating, using an artificial intelligence algorithm, based on the at least one database, a first plurality of current best traits shared by the plurality of members of the particular group;
   for each particular member of the plurality of members of the particular group that includes the particular user:
      displaying, by the data processing hardware, on a corresponding display of a corresponding electronic device associated with the particular member, a plurality of self-assessment interface elements each corresponding to a selectable current best trait of the first plurality of current best traits; and
      receiving, at the data processing hardware, from the corresponding electronic device associated with the particular member, one or more corresponding self-assessment selection inputs, each self-assessment selection input corresponding to selection of a particular self-assessment interface element of the plurality of self-assessment interface elements that corresponds to a particular current best trait of the first plurality of current best traits that the particular member self-identifies as wanting to possess;
   based on the self-assessment selection inputs received from the plurality of members of the particular group that includes the particular user:
      generating, by the data processing hardware, using the artificial intelligence algorithm, based on the at least one database, a plurality of words, wherein each word of the plurality of words represents a particular one of the first plurality of current best traits that one or more of the plurality of members self-identified as wanting to possess; and
      for each corresponding word of the plurality of words, determining, by the data processing hardware, a frequency that the particular current best trait represented by the corresponding word was selected by the plurality of members; and
   for each particular member of the plurality of members of the particular group that includes the particular user, displaying, by the data processing hardware, on the corresponding display of the corresponding electronic device associated with the particular member, a group-level visualization interface including a word cloud of the plurality of words, the word cloud of the plurality of words graphically representing the frequencies that the current best traits represented by the plurality of words were selected by the plurality of members such that each word of the plurality of words in the word cloud comprises a respective size that corresponds to the frequency that the particular best trait represented by the corresponding word was selected by the plurality of members.

2. The method of claim 1, wherein the group-level visualization interface is updated in real time.

3. The method of claim 1, wherein the respective size of each corresponding word of the plurality of words in the word cloud increases as the frequency that the particular current best trait represented by the corresponding word was selected by the plurality of members.

4. The method of claim 1, wherein the method further comprises, in response to receiving the one or more self-assessment selection inputs, displaying on the display a constellation, the constellation generated based on data corresponding to the one or more self-assessment selection inputs.

5. An electronic device comprising:
   a display associated with a user;
   an input device;
   one or more processors; and
   memory in communication with the one or more processors and storing one or more programs that, when executed on the one or more processors, cause the one or more processors to perform operations comprising:
      displaying, on the display, a purposeful inquiry interface including a plurality of navigation elements, each of the plurality of navigation elements corresponding to a self-identified level of purposefulness, wherein the plurality of navigation elements includes a first navigation element corresponding to an explore interface and a second navigation element corresponding to a reflection interface;
      while displaying the purposeful inquiry interface, receiving, via the input device, from the user, a first navigation selection input corresponding to selection of the first navigation element;
      in response to receiving the first navigation selection input:
         interfacing with at least one database comprising a group-level dataset for a particular group that includes the user, the group-level dataset for the particular group comprising corresponding activities for each particular member of the particular group that the particular member has self-identified as having improved their respective purposefulness;

generating, using an artificial intelligence algorithm, based on the at least one database, a plurality of explore interface elements, each explore interface element corresponding to a selectable activity that is self-identified by members of the particular group as having improved their respective purposefulness; and displaying, on the display, the explore interface, the explore interface including the plurality of explore interface elements, each explore interface element corresponding to a particular activity;

while displaying the explore interface, receiving, via the input device, from the user, one or more explore selection inputs, the one or more explore selection inputs corresponding to a particular explore interface element;

in response to receiving the one or more explore selection inputs, storing data associated with the one or more explore selection inputs in the at least one database;

while displaying the purposeful inquiry interface, receiving, via the input device, from the user, a second navigation selection input corresponding to selection of the second navigation element;

in response to receiving the second navigation selection input, displaying, on the display, the reflection interface, the reflection interface including a plurality of reflection improvement interface elements each associated with a corresponding trait that the user would want to work on improving;

receiving, via the input device, from the user, a reflection improvement input indicating selection of a particular reflection improvement interface element of the plurality of reflection improvement interface elements that is associated with the corresponding trait that the user self-identifies as wanting to work on improving;

in response to receiving the reflection improvement input, displaying, on the display, a reflection elaboration interface;

while displaying the reflection elaboration interface:
providing, for display in the reflection elaboration interface, an inquiry message prompting the user to input text indicating why the user wants to work on improving the corresponding trait associated with the particular reflection improvement interface that the user self-identified as want to working on improving; and receiving, in the reflection elaboration interface, from the user, a free-form text input including free-form text indicating why working on improving the corresponding trait is important to the user;

processing, using natural language processing through artificial intelligence, the free-form text to determine a plurality of follow-up reflections each associated with a particular activity the user can engage into align with their best self for improving the corresponding trait; and displaying, on the display, the plurality of follow-up reflections.

6. The electronic device of claim 5, wherein the operations further comprise, in response to receiving the one or more explore selection inputs, generating for display, one or more actions list interface elements, each one or more actions list interface element corresponding to each of the one or more explore selection inputs.

7. The electronic device of claim 6, wherein the plurality of navigation elements further includes a third navigation element corresponding to an action interface.

8. The electronic device of claim 7, wherein the operations further comprise, responsive to receiving, via the input device, a third navigation selection input, displaying on the display, the action interface, wherein the action interface includes one or more action interface elements corresponding to a particular activity.

9. The electronic device of claim 8, wherein the one or more action interface elements include the one or more action interface elements.

10. The electronic device of claim 8, wherein the at least one database includes an individualized dataset, and wherein the one or more action interface elements include one or more AI-generated action interface elements, wherein the one or more AI-generated action interface elements are generated based on the individualized dataset.

11. The electronic device of claim 8, wherein the one or more action interface elements include one or more AI-generated action interface elements, wherein the one or more AI-generated action interface elements are generated based on the group-level dataset.

12. The electronic device of claim 5, wherein the operations further comprise, in response to storing data associated with the one or more explore selection inputs, generating for display one or more new explore interface elements.

13. The electronic device of claim 12, wherein the one or more new explore interface elements are displayed when the explore interface is refreshed.

14. The electronic device of claim 5, wherein the operations further comprise, in response to receiving the one or more explore selection inputs, generating, for display, one or more new explore interface elements.

15. The electronic device of claim 14, wherein the one or more new explore interface elements are displayed when the explore interface is refreshed.

16. The electronic device of claim 5, wherein the at least one database includes an individualized dataset, and wherein the explore interface elements include individualized interface elements, the individualized interface elements generated based on data from the individualized dataset.

17. The electronic device of claim 5, wherein the explore interface elements include group-level interface elements, the group-level interface elements generated based on data from the group-level dataset.

18. The electronic device of claim 5, wherein the purposeful inquiry interface includes a welcome message, the welcome message generated based on data stored in the at least one database.

* * * * *